(12) United States Patent
Cortez, Jr. et al.

(10) Patent No.: US 12,285,563 B2
(45) Date of Patent: Apr. 29, 2025

(54) CANNULA DEVICE FOR HIGH FLOW THERAPY

(71) Applicant: Vapotherm, Inc., Exeter, NH (US)

(72) Inventors: Felino V. Cortez, Jr., Bowie, MD (US); George C. Dungan, II, Dallas, TX (US); Mark Kolnsberg, Beverly, MA (US); Charles Busey, Easton, MD (US); Randolph Brian Kirkland, Asheville, NC (US); Karen Goldwalker, Greenland, NH (US); Meghan H. Kate, Deerfield, NH (US)

(73) Assignee: VAPOTHERM, INC., Exeter, NH (US)

( * ) Notice: Subject to any disclaimer, the term of this patent is extended or adjusted under 35 U.S.C. 154(b) by 363 days.

(21) Appl. No.: 17/680,576

(22) Filed: Feb. 25, 2022

(65) Prior Publication Data

US 2023/0026216 A1 Jan. 26, 2023

Related U.S. Application Data

(63) Continuation of application No. 15/637,556, filed on Jun. 29, 2017, now Pat. No. 11,291,789.
(Continued)

(51) Int. Cl.
*A61M 16/06* (2006.01)
*A61M 16/00* (2006.01)
(Continued)

(52) U.S. Cl.
CPC .... *A61M 16/0666* (2013.01); *A61M 16/0069* (2014.02); *A61M 16/0683* (2013.01);
(Continued)

(58) Field of Classification Search
CPC .............. A61M 16/06; A61M 16/0666; A61M 16/0677; A61M 16/0069; A61M 16/0858;
(Continued)

(56) References Cited

U.S. PATENT DOCUMENTS

| RE24,534 E | 9/1958 | Dahl |
|---|---|---|
| 2,941,544 A | 6/1960 | Lucien |

(Continued)

FOREIGN PATENT DOCUMENTS

| AU | 2013212314 | 11/2017 |
|---|---|---|
| AU | 2013337995 | 6/2018 |

(Continued)

OTHER PUBLICATIONS

RBC Aerospace Bearings, "Plain Bearings" Spec Sheet, 2016, p. 43 (Year: 2016).*
(Continued)

*Primary Examiner* — Bradley H Philips
*Assistant Examiner* — Savannah L Gabriel
(74) *Attorney, Agent, or Firm* — McDermott Will & Emery LLP

(57) ABSTRACT

A nasal cannula is described herein for respiratory therapy which includes a first gas supply tub with a distal end terminating in a first connector, and a nasal cannula body which includes a first end rotatably coupled to the first connector, a second end opposite the first end, a longitudinal axis extending from the first end to the second end, and a first nasal prong in fluid communication with the first gas supply tube. The first nasal prong is rotatable relative to the first gas supply tube about the longitudinal axis of the nasal cannula body.

22 Claims, 15 Drawing Sheets

Related U.S. Application Data

(60) Provisional application No. 62/356,774, filed on Jun. 30, 2016.

(51) Int. Cl.
*A61M 16/08* (2006.01)
*A61M 16/14* (2006.01)

(52) U.S. Cl.
CPC ........ *A61M 16/0858* (2014.02); *A61M 16/14* (2013.01); *A61M 16/0672* (2014.02); *A61M 16/0816* (2013.01)

(58) Field of Classification Search
CPC .............. A61M 16/0683; A61M 16/14; A61M 16/0672; A61M 16/0816; A61M 16/0605; A61M 2025/0226; A61M 2016/0661
See application file for complete search history.

(56) References Cited

U.S. PATENT DOCUMENTS

| | | | |
|---|---|---|---|
| 4,003,398 A | | 1/1977 | Duveau |
| 4,422,456 A | * | 12/1983 | Tiep .................. A61M 16/0666 128/207.18 |
| 4,708,166 A | | 11/1987 | Kobold |
| 4,782,832 A | | 11/1988 | Trimble |
| 4,790,308 A | | 12/1988 | Weichselbuam |
| 5,099,836 A | | 3/1992 | Rowland |
| 5,113,911 A | | 5/1992 | Hirsh |
| 5,433,242 A | | 7/1995 | Buchtel |
| 6,561,188 B1 | | 5/2003 | Ellis |
| 6,805,126 B2 | | 10/2004 | Dutkiewicz |
| 6,986,353 B2 | | 1/2006 | Wright |
| 7,007,694 B2 | | 3/2006 | Aylsworth et al. |
| 7,481,244 B2 | | 1/2009 | Bivin |
| 7,662,181 B2 | | 2/2010 | Deem |
| 7,743,770 B2 | | 6/2010 | Curti |
| 7,832,400 B2 | | 11/2010 | Curti et al. |
| 8,631,799 B2 | | 11/2014 | Davenport |
| 9,333,317 B2 | | 5/2016 | Cortez, Jr. et al. |
| 9,597,263 B2 | | 3/2017 | Visveshwara |
| 9,822,515 B2 | | 11/2017 | Wu |
| 9,925,348 B2 | | 3/2018 | Payton et al. |
| 10,100,622 B2 | | 10/2018 | Gonzalez |
| 10,265,494 B2 | | 4/2019 | Cortez, Jr. et al. |
| 10,300,236 B2 | | 5/2019 | Cortez, Jr. et al. |
| 2004/0112383 A1 | | 6/2004 | Curti |
| 2004/0226566 A1 | * | 11/2004 | Gunaratnam ..... A61M 16/0825 128/207.18 |
| 2005/0028822 A1 | | 2/2005 | Sleeper et al. |
| 2005/0066976 A1 | | 3/2005 | Wondka |
| 2005/0103347 A1 | | 5/2005 | Curti et al. |
| 2005/0229927 A1 | | 10/2005 | Fink et al. |
| 2005/0229928 A1 | | 10/2005 | Irvi |
| 2006/0030696 A1 | | 2/2006 | Klenner |
| 2006/0180151 A1 | * | 8/2006 | Rinaldi ............. A61M 16/0666 128/207.18 |
| 2006/0230929 A1 | | 10/2006 | Bliss |
| 2006/0230931 A1 | | 10/2006 | Bliss |
| 2007/0175473 A1 | | 8/2007 | Lewis et al. |
| 2008/0121230 A1 | | 5/2008 | Cortez et al. |
| 2008/0223375 A1 | | 9/2008 | Cortez, Jr. et al. |
| 2009/0044808 A1 | | 2/2009 | Guney |
| 2009/0101147 A1 | | 4/2009 | Landis |
| 2009/0250132 A1 | | 10/2009 | Bivin |
| 2009/0253995 A1 | | 10/2009 | Lewis et al. |
| 2010/0096019 A1 | | 4/2010 | DiPerna |
| 2010/0108073 A1 | | 5/2010 | Zollinger et al. |
| 2010/0113955 A1 | | 5/2010 | Colman |
| 2010/0252037 A1 | | 10/2010 | Wondka |
| 2010/0282247 A1 | | 11/2010 | Kadrichu |
| 2011/0067704 A1 | * | 3/2011 | Kooij ................ A61M 16/0858 128/207.18 |
| 2011/0073116 A1 | | 3/2011 | Genger |
| 2011/0094518 A1 | | 4/2011 | Cipollone |
| 2011/0146685 A1 | | 6/2011 | Allan et al. |
| 2011/0232649 A1 | | 9/2011 | Collazo et al. |
| 2011/0270166 A1 | * | 11/2011 | Martin ................... A61H 21/00 604/79 |
| 2011/0284001 A1 | | 11/2011 | Tero |
| 2012/0090622 A1 | | 4/2012 | Chang |
| 2012/0125332 A1 | | 5/2012 | Niland |
| 2012/0167878 A1 | | 7/2012 | Belson |
| 2012/0304992 A1 | | 12/2012 | Ratto |
| 2012/0304999 A1 | * | 12/2012 | Swift .................. A61M 16/06 128/205.25 |
| 2013/0008447 A1 | | 1/2013 | Gunaratnam et al. |
| 2013/0092165 A1 | | 4/2013 | Wondka |
| 2013/0146064 A1 | * | 6/2013 | Dryden ................ A61M 15/08 128/207.18 |
| 2013/0152925 A1 | | 6/2013 | Rahmel et al. |
| 2013/0160772 A1 | | 6/2013 | Tabrizchi |
| 2013/0186395 A1 | | 7/2013 | Cortez, Jr. et al. |
| 2013/0230674 A1 | * | 9/2013 | Curti ................ A61M 16/0683 428/34.1 |
| 2014/0066801 A1 | | 3/2014 | Tero |
| 2014/0094669 A1 | * | 4/2014 | Jaffe ................ A61M 16/0858 128/207.18 |
| 2014/0116447 A1 | | 5/2014 | Cortez, Jr. et al. |
| 2014/0137744 A1 | | 5/2014 | Wilkinson |
| 2014/0147506 A1 | | 5/2014 | Longest et al. |
| 2014/0150789 A1 | | 6/2014 | Flanagan et al. |
| 2014/0158127 A1 | | 6/2014 | Boucher et al. |
| 2014/0166009 A1 | | 6/2014 | Flanagan et al. |
| 2014/0230942 A1 | | 8/2014 | Takai |
| 2014/0261704 A1 | | 9/2014 | Hoogenakker |
| 2014/0366885 A1 | | 12/2014 | Haibach |
| 2015/0000654 A1 | | 1/2015 | Martin |
| 2015/0000659 A1 | | 1/2015 | Martin |
| 2015/0000660 A1 | | 1/2015 | Martin |
| 2015/0090255 A1 | | 4/2015 | Gulliver |
| 2015/0230731 A1 | | 8/2015 | Levitsky |
| 2016/0015296 A1 | | 1/2016 | Garaycochea |
| 2016/0015921 A1 | | 1/2016 | Harrison |
| 2016/0030696 A1 | * | 2/2016 | Klenner ............ A61M 16/0875 128/207.18 |
| 2016/0158476 A1 | | 6/2016 | Tatkov |
| 2016/0271353 A1 | | 9/2016 | Cheung |
| 2017/0000965 A1 | | 1/2017 | Cortez et al. |
| 2017/0348500 A1 | * | 12/2017 | Johnson ............ A61M 16/0688 |
| 2018/0064898 A1 | * | 3/2018 | Evans ................ A61M 16/0875 |
| 2019/0328990 A1 | | 10/2019 | Cortez et al. |
| 2019/0328993 A1 | | 10/2019 | Cortez et al. |

FOREIGN PATENT DOCUMENTS

| | | |
|---|---|---|
| AU | 2017251790 | 3/2020 |
| EP | 2022528 | 2/2009 |
| EP | 2247331 | 11/2010 |
| EP | 2806926 | 5/2017 |
| EP | 2914322 | 12/2018 |
| EP | 3646913 | 5/2020 |
| EP | 3216475 | 7/2020 |
| EP | 3747488 | 12/2020 |
| FR | 2827778 A1 | 1/2003 |
| JP | 2018089139 | 5/2018 |
| WO | WO-9818513 | 5/1998 |
| WO | WO-2006138579 | 12/2006 |
| WO | WO-2008060587 | 5/2008 |
| WO | WO2009094532 | 7/2009 |
| WO | WO-2013041996 | 3/2013 |
| WO | WO-2013042004 | 3/2013 |
| WO | WO-2013112545 | 8/2013 |
| WO | WO-2013157960 | 10/2013 |
| WO | WO-2014070833 | 5/2014 |
| WO | WO-2014142681 | 9/2014 |
| WO | WO-2015121815 | 8/2015 |
| WO | WO-2015164921 | 11/2015 |
| WO | WO-2016043607 | 3/2016 |
| WO | WO-2017062677 | 4/2017 |
| WO | WO-2018005851 | 1/2018 |

(56) References Cited

FOREIGN PATENT DOCUMENTS

| WO | WO-2018065588 | 4/2018 |
|---|---|---|
| WO | WO-2018068085 | 4/2018 |
| WO | WO-2019191814 | 10/2019 |

OTHER PUBLICATIONS

International Search Report and Written Opinion for PCT/US2016/040465 dated Oct. 4, 2016 (16 pages).
International Search Report and Written Opinion for PCT/US2017/040079 dated Oct. 18, 2017 (21 pages).
International Search Report and Written Opinion for PCTUS2018/049979 dated Nov. 23, 21018 (16 pages).
International Search Report and Written Opinion for PCT/US2020/039641 dated Oct. 7, 2020 (13 pages).
International Search Report and Written Opinion for PCT/US2021/051987 dated Jan. 5, 2022 (19 pages).
Doshi et al., "High-Velocity Nasal Insufflation in the Treatment of Respiratory Failure: A Randomized Clinical Trial", Annals of Emergency Medicine, Jul. 2017;72(1):73-83.
Spivey S., et al., "Assessment of High Flow Nasal Cannula Therapy use in the Emergency Department Setting: Observations of Practice Across Four Systems", Respiratory Therapy, vol. 10, No. 1, pp. 30-34 (2015).
U.S. Appl. No. 15/199,158, filed Jun. 30, 2016.
U.S. Appl. No. 15/637,556, filed Jun. 29, 2017.
U.S. Appl. No. 16/124,818, filed Sep. 7, 2018.
U.S. Appl. No. 18/214,740, filed Jun. 27, 2023.
U.S. Appl. No. 16/912,095, filed Jun. 25, 2020.
U.S. Appl. No. 17/484,374, filed Sep. 24, 2021.

\* cited by examiner

CANNULA DEVICE FOR HIGH FLOW THERAPY

CROSS-REFERENCE TO RELATED APPLICATIONS

This application is a continuation of U.S. patent application Ser. No. 15/637,556, filed on Jun. 29, 2017 (now U.S. Pat. No. 11,291,789), which claims the priority to and the benefit of U.S. Provisional Patent Application No. 62/356,774, filed on Jun. 30, 2016, the contents of which are hereby incorporated by reference in their entirety.

BACKGROUND

Patients with respiratory ailments may be treated with respiratory assist devices, for example, devices that deliver supplemental breathing gas to a patient. Such devices may deliver gas to a patient using high flow therapy ("HFT"). HFT devices deliver a high flow rate of breathing gas to a patient via an interface such as a nasal cannula to increase a patient's fraction of inspired oxygen (FiO2), decrease a patient's work of breathing, or to do both. Nasal cannulae are commonly used in acute short-term therapy and in therapy for chronic issues.

Nasal cannulae generally have a single geometry for the insertion angle of the nasal prongs into a patient's nares. However, amongst a population of patients there is variability in the anatomy of the nares, nasal cavity and facial structures surrounding the nares. Furthermore, nasal cannulae often provide only one directional mode and can be difficult to affix on a patient in alternative orientations. As a result, in some patients, the nasal prongs of a nasal cannula abut sensitive tissues within the nasal cavity and the stream of breathing gas is directed into the tissues rather than into the nasal passageways, diminishing the effects of treatment and causing irritation of sensitive tissues or structures and mucous membranes. Improper positioning of nasal prongs within the nares of a patient can result in inadequate upper airway flush and reduce effectiveness of respiratory therapies. To fit nasal prongs to a patient, sometimes nasal cannula prongs are cut with a scissors in medical environments to change the size, length, and/or angle of the prongs, but this often leaves the prongs with sharp edges that can further irritate or damage sensitive tissues within the nasal cavity. Furthermore, nasal cannulae used for respiratory therapies may need to be removed in order to clean secretions around a nare, unblock an occluded nare or administer other medical therapies which require access to a patient's nare. Removal of the nasal cannula prongs from the nare stops the respiratory therapy.

Using current methods of restraining and orienting gas supply tubing for use with nasal cannulae, patient movement and adjustments to the gas supply tubes can cause rubbing and skin irritation and can lead to misalignment or poor orientation of the nasal prongs within the nares. In some instances, movement of a gas supply tube can cause jostling of the nasal cannula leading to the nasal prongs being poorly oriented in the nares and causing irritation and loss of efficiency of respiratory therapy. In other instances, movement of the nasal cannula, for example, due to a patient talking, eating or otherwise moving, causes motion of the gas supply tubes which may rub on or around the patient's ears also causing irritation and potential damage. In many instances, and in particular for pediatric patients and neonates receiving respiratory therapies, patients depend on the respiratory therapy to maintain proper oxygen and ventilation status. Therapy is often effective as long as the nasal prongs remain properly positioned within the nares. Methods of affixing gas supply tubes to maintain a proper orientation of the prongs, including medical tape and polymeric wound adhesives, are often difficult to remove or replace, inadequately affix the tubing and cause irritation or damage to a patient's skin.

Trauma from the nasal cannula can occur during long-term therapies (e.g., periods greater than seven days of continuous use) and may include the development of medical device-related pressure ulcers (MDRPU). The gas supply tubing may be pliable and soft when not pressurized, but may become distended under internal pressure and warm due to the passage of heated gas through the tubing. The rubbing of the hard tubing around the ears may lead to vascular compression of the dermal capillary bed as well as abrasive surface trauma. The warmth of the tubing may cause sweating and exacerbate the irritation and skin breakdown. If worn too tightly, over long periods, the supply tubing can cause undue pressure and friction about the ears and at other points of contact with a patient's skin. In some cases, rubbing of the supply tubing over the ear may lead to the development of pressure ulcers in the posterior ear and temporomastoid area behind the ear and along the path of the nasal cannula gas supply tubing.

SUMMARY

Accordingly, disclosed herein are systems, methods, and devices providing enhanced patient comfort in systems relating to nasal cannulae for respiratory therapy. For example, a nasal cannula with rotatably adjustable prongs is described below that allows a patient or health care professional to rotate the prong to ensure heated and humidified breathing gas is directed from the outlet of the nasal prong and into the nasal passageway rather than into the mucosa. Rotatable prongs also allow a health care professional to rotate one or both prongs out of the nare to rest the nare, clean secretions around the nare and/or access the nare for an alternate purpose. In particular, for infant nasal cannulae, the ability to rotate one or both prongs out of the nares allows a health care professional to insert a feeding tube into one of the nares while continuing respiratory therapy at the other nare.

Additionally or alternatively, a nasal cannula with a stable orientation below the nares, which simultaneously allows rotational relief of the prongs within the nares, allows the nasal cannula to be fit to the anatomies of a variety of patients and increases the comfort of patients in both short and long-term therapies. A nasal cannula assembly with the capability of rotational nasal prong adjustment in the nares prevents tissue irritation and abrasion of nasal passageways caused by direct contact of the nasal prong against sensitive tissues in the nare and nasal cavity. The rotational adjustment of the prongs also directs gas flow into the nasal passageway and away from sensitive tissue.

In another example, nasal cannulae with adjustable distance between the nasal prongs are described. The adjustable distance between the prongs allows the nasal cannula to be fit to a variety of patient sizes and anatomies with minimal irritation to sensitive tissues in the nasal passage. Furthermore, adjustment of the distance between prongs allows a health care professional to position the prongs in the center of the nare to optimize the flow of breathing gas into the nasal passageway for optimal upper airway flush.

In another example, a variety of fastening mechanisms for affixing gas supply tubes and a nasal cannula on a patient are described. A swivel connector that does not transfer torque from the gas supply tubes to the nasal cannula is described. A tubing guide is described, which affixes a gas supply tube to a patient's skin with a removable adhesive pad. The tubing guide is configured such that the gas supply tube may be removed from the tubing guide and the gas supply tube will have the proper orientation upon replacement. A slidable connector is described for retaining two gas supply tubes below a patient's chin without kinking.

Various strap systems are also described, which hold the nasal cannula in a proper position on a patient's face to ensure efficient delivery of respiratory therapy into the patient's nares. Simultaneously, the strap systems prevent chafing, irritation, and ulceration of the sensitive skin on and around the ears by holding the gas supply tubes away from the ears or otherwise protecting the ears. Gas supply tubes become hard when they are pressurized by the passage of breathing gas through them, and may be warm, causing sweating and leading to faster breakdown of the skin where the tubes rub against bony protrusions around the ears. Preventing the rubbing of gas supply tubes against the ears increases patient comfort and decreases risk of developing an MDRPU, while ensuring that the nasal cannula is secured to the patient for delivery of respiratory therapy.

In one aspect, a nasal cannula for respiratory therapy includes a first gas supply tube with a distal end terminating in a first connector, and a nasal cannula body that includes a first end rotatably coupled to the first connector, a second end opposite the first end, a longitudinal axis extending from the first end to the second end, and a first nasal prong in fluid communication with the first gas supply tube. The first nasal prong is rotatable relative to the first gas supply tube about the longitudinal axis of the nasal cannula body.

The means for the rotatable coupling may vary. For example, in some implementations, the rotatable coupling between the first end of the nasal cannula body and the first connector is a bearing. In some implementations, the rotatable coupling between the first end of the nasal cannula body and the first connector is a journal bearing. Furthermore, the journal bearing may provide varying amounts of static frictional torque. For example, in some implementations, the journal bearing has sufficient static frictional torque to maintain a rotational position of the first nasal prong relative to the first gas supply tube. In some implementations, the journal bearing has a frictional torque of about 0.1 Nm to 1 Nm. Additionally or alternatively, in some implementations, the journal bearing has an internal surface contoured such that the journal bearing has intermittent rotational stops. Additionally or alternatively, in some implementations, the nasal cannula also includes a lock configured to lock a rotational position of the first nasal prong relative to the first gas supply tube.

The number of nasal prongs extending from the nasal cannula may vary. For example, in some implementations, the nasal cannula body may include a second nasal prong, in addition to a first nasal prong. Furthermore, the second nasal prong may be rotatable. For example, in some implementations, the second nasal prong is rotatable relative to the first gas supply tube about the longitudinal axis of the nasal cannula body. In some implementations, the first prong is rotatable relative to the second nasal prong about the longitudinal axis of the nasal cannula body. Additionally or alternatively, the location and/or arrangement of the nasal prongs may vary. For example, in some implementations, the nasal cannula body includes a first section and a second section disposed adjacently along the longitudinal axis of the nasal cannula body, and the first nasal prong is disposed on the first section and the second nasal prong is disposed on the second section. In some implementations, the first section and the second section are coupled by a journal bearing, and the first section is rotatable about the longitudinal axis of the nasal cannula body relative to the second section.

The number and/or arrangement of gas supply tubes may vary. For example, in some implementations, the nasal cannula includes a second gas supply tube with a distal end that terminates in a second connector, and the second end of the nasal cannula body is rotatably coupled to the second connector. In some implementations, the second nasal prong is in fluid communication with the second gas supply tube. In other implementations, the first nasal prong is not in fluid communication with the second prong. In some implementations, the first nasal prong and the second nasal prong are joined by a solid bridge connector. Additionally or alternatively, in some implementations, the nasal cannula body is detachable from the first supply tube.

The arrangement of and/or distance between the nasal prongs may vary. In some implementations, the nasal cannula body includes a surface contoured to provide a discrete number of stable axial positions of the first nasal prong. Additionally or alternatively, in some implementations, an axial distance between the first nasal prong and the second nasal prong along the longitudinal axis of the nasal cannula body is adjustable. In some implementations, the first nasal prong is axially slidable along the longitudinal axis of the nasal cannula body relative to the second nasal prong.

The flow rate of the breathing gas in the nasal cannula may vary. In some implementations, the nasal cannula includes a gas source wherein the gas source is configured to provide breathing gas at a flow rate of over 8 liters per minute (LPM) (e.g., 10 LPM, 15 LPM, etc.). Additionally or alternatively, the nasal cannula may work with various components for delivering the breathing gas to the patient. For example, in some implementations, the first connector includes a first section sized to receive the first gas supply tube and a second section sized for insertion into the first end of the nasal cannula body. The first section is coupled to the second section at a bearing, and the second section is configured to swivel relative to the first section. Additionally or alternatively, in some implementations, the nasal cannula includes a slidable connector that has a body, a first opening sized to receive two supply tubes, a second opening sized to receive a single supply tube, a third opening sized to receive a single supply tube, and a wedge disposed between the second and third openings. The first gas supply tube passes through the first and second openings, and the second gas supply tube extends through the first and third openings. The second and third openings are offset such that the first and second gas supply tubes diverge in exiting the second and third openings. Additionally or alternatively, in some implementations, the nasal cannula has a tubing guide with a flexible body and a guide connector coupled to a first side of the flexible body. The guide connector has a first opening and a second opening opposite the first opening, each sized to receive a gas supply tube. The first gas supply tube passes through the first opening and the second opening, and the flexible body includes a second side coated in a biocompatible adhesive. In some implementations, the nasal cannula includes an elastomeric loop having a connector detachably coupled to a gas supply tube. The connector is coupled non-fluidically to the first gas supply tube, and the elastomeric loop is sized to hang over an ear.

In another aspect, a kit for a high flow therapy system includes a nasal cannula. The nasal cannula includes a nasal cannula body and a first gas supply tube that has a distal end terminating in a first connector. The nasal cannula body also includes a first end rotatably coupled to the first connector, a second end opposite the first end, a longitudinal axis extending from the first end to the second end, and a first nasal prong in fluid communication with the first gas supply. The first nasal prong is rotatable relative to the first gas supply tube about the longitudinal axis of the nasal cannula body.

The means for the rotatable coupling may vary. For example, in some implementations, the rotatable coupling between the first end of the nasal cannula body and the first connector is a bearing. In some implementations, the rotatable coupling between the first end of the nasal cannula body and the first connector is a journal bearing. The journal bearing may provide varying amounts of static frictional torque. For example, in some implementations, the journal bearing has sufficient static frictional torque to maintain a rotational position of the first nasal prong relative to the first gas supply tube. In certain implementations, the journal bearing has a frictional torque of about 0.1 Nm to 1 Nm. Additionally or alternatively, the journal bearing has an internal surface contoured such that the journal bearing has intermittent rotational stops.

A variety of fastening mechanisms may be provided with the kit or used with the kit to comfortably secure the nasal cannula and supply tubes on a patient. For example, in some implementations, the kit includes a fastening mechanism that is configured to secure the nasal cannula and the first gas supply tube on a patient during use. In some implementations, the fastening mechanism includes a fabric encasement sized to cover a length of the first gas supply tube that extends over a patient's ear. Additionally or alternatively, in some implementations, the fabric encasement includes a wire structure within the fabric disposed circumferentially around the length of the first gas supply tube that extends over a patient's ear. The wire structure is configured to hold the length of the first gas supply tube away from the patient's ear. The fabric comprising the fabric encasement may vary. For example, in some implementations, the fabric encasement is a wicking fabric and a low-friction fabric. In other implementations, the fabric encasement is a silicone encasement sized to cover a length of the first gas supply tube that extends over a patient's ear.

Additionally or alternatively, in some implementations, the fastening mechanism comprises a strap sized to extend around a backside of a patient's head. The strap has a first end and a second end, the first end of the strap coupled to the first gas supply tube above a first ear of the patient and the second end of the strap coupled to a second gas supply tube above a second ear of the patient. The first gas supply tube and the second gas supply tube are secured above the first ear and above the second ear. Additionally, or alternatively, in some implementations, the strap is coupled to the first gas supply tube by an adjustable securing mechanism at the first end of the strap. In some implementations, the first end of the strap comprises a raised section having a groove around the edge of the raised section sized to receive the first gas supply tube.

Additionally, or alternatively, in some implementations, the fastening mechanism includes a band configured to be coupled to the first gas supply tube above the first ear of the patient and to be coupled to the second gas supply tube above the second ear of the patient. The band is sized to extend over a top of the patient's head. In some implementations, the strap is coupled to the band.

Additionally or alternatively, in some implementations, the fastening mechanism comprises an elastomeric loop having a connector detachably coupled to the first gas supply tube. The connector is coupled non-fluidically to the first gas supply tube and the elastomeric loop is sized to hang over an ear. In some implementations, the elastomeric loop is configured to be coupled to the first gas supply tube at a coupler configured to be positioned at a bottom point of the elastomeric loop. Furthermore, the elastomeric loop may be covered to provide additional comfort or support to the ear. For example, in some implementations, the elastomeric loop includes a loop encasement covering the elastomeric loop and configured to be disposed between the ear loop and the patient's ear. In some implementations, the loop encasement includes a fluid-filled cushion or foam.

Additionally or alternatively, in some implementations, the fastening mechanism has a tubing guide with a flexible body and a guide connector coupled to a first side of the flexible body. The guide connector has a first opening and a second opening opposite the first opening, each sized to receive a gas supply tube. The first gas supply tube passes through the first opening and the second opening, and the flexible body includes a second side coated in a biocompatible adhesive. Additionally or alternatively, in some implementations, the first gas supply tube includes a first lumen configured to receive the breathing gas and a second lumen encompassing the first lumen configured to receive cooled gas. In some implementations, a second gas supply tube is coupled to the second end of the nasal cannula body.

Additionally or alternatively, the nasal cannula may work with various components for delivering the breathing gas to the patient. For example, in some implementations, the kit includes a slidable connector that has a body, a first opening sized to receive two supply tubes, a second opening sized to receive a single supply tube, a third opening sized to receive a single supply tube, and a wedge disposed between the second and third openings. The first gas supply passes through the first and second openings and the second gas supply tube extending through the first and third openings. The second and third openings are offset such that the first and second gas supply tubes diverge exiting the second and third openings. Additionally or alternatively, in some implementations, the first connector includes a first section sized to receive the first gas supply tube and a second section sized for insertion into the first end of the nasal cannula body. The first section is coupled to the second section at a bearing and the second section is configured to swivel relative to the first section. In some implementations, the connector is configured to allow the second section 360° of rotation relative to the first section. The flow rate of the breathing gas in the nasal cannula may vary. In some implementations, the kit includes a gas source configured to provide breathing gas at a flow rate of over 8 LPM (e.g., 10 LPM, 15 LPM, etc.). In other implementations, the gas source is configured to provide breathing gas at a flow rate of over 20 LPM (e.g., 22 LPM, 25 LPM, 27 LPM, etc.).

The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the systems, methods, and devices described herein, certain illustrative embodiments will be described. Although the embodiments and features described herein are specifically described for use in connection with a high flow therapy system, it will be understood that all the components and other features outlined below may be combined with one another in any suitable manner and may be adapted and applied to other types of respiratory therapy and respiratory therapy devices, including low flow oxygen therapy, continuous positive airway pressure therapy (CPAP), mechanical ventilation, oxygen masks, Venturi masks, and Tracheostomy masks. Furthermore, it should be noted that while certain embodiments are discussed herein within regards to increasing a patient's comfort through varying means (e.g., nasal cannula prong arrangement, fastening mechanism, etc.), these various embodiments may be used in various combinations to increase a patient's overall level of comfort during treatment.

The systems and devices described herein increase patient comfort during respiratory therapies by ensuring a good fit between the patient's anatomy and the nasal cannula prongs while protecting sensitive tissues from irritation. Devices that allow adjustment of prong orientation within the nares allow proper delivery of respiratory therapy into the nasal cavity and optimize flushing of the upper respiratory tract. Ill-fitting nasal prongs can irritate sensitive tissues within the nare and can direct breathing gas into these tissues and mucosa, causing discomfort as well as decreasing the efficacy of therapies. By allowing a user to adjust the orientation of the nasal prongs within the nares with rotatable prongs and/or adjustment of the distance between nasal prongs, the nasal prongs may be properly positioned to provide comfortable therapy to the patient.

Devices that affix the nasal cannula on the patient's face include fastening mechanisms that hold the gas supply tubes away from a patient's ears. Warm or pressurized gas supply tubes that are looped over the ears can cause irritation and ulceration of the sensitive tissues and bony protrusions about the ear. By securing the gas supply tubes away from the ears, the nasal cannula and gas supply tubes are secured in position on the patient's face without causing irritation to the ears. Devices that retain the gas supply tubes from interfering or irritating the patient also increase patient comfort and ensure that the nasal cannula remains properly positioned for delivery of respiratory therapy.

Figure 1:
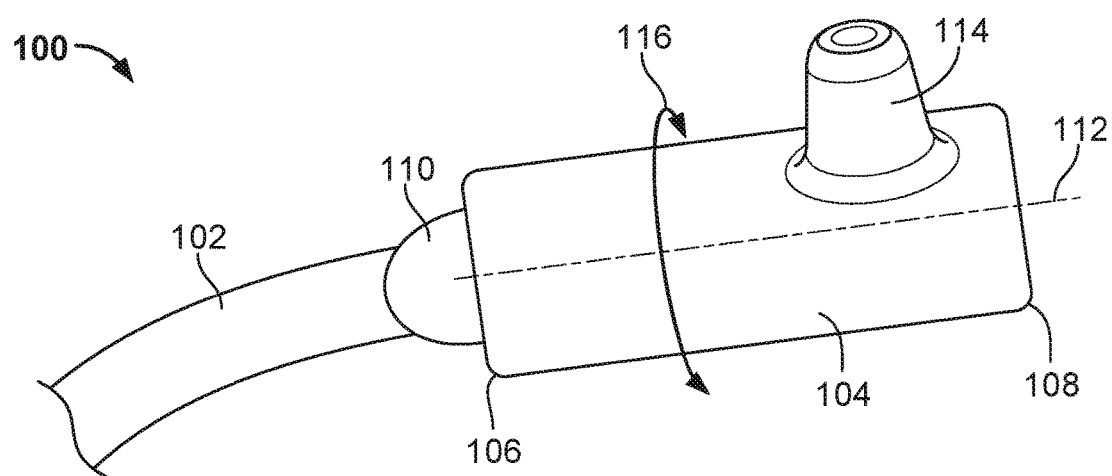
FIG. 1 shows an illustrative nasal cannula for respiratory therapy.

FIG. 1 shows an illustrative nasal cannula 100 for respiratory therapy. Nasal cannula 100 includes nasal cannula body 104, first end 106, second end 108, first gas supply tube 102, first connector 110, longitudinal axis 112 of nasal cannula body 104, and first nasal prong 114. First gas supply tube 102 is rotatably connected to first end 106 of nasal cannula body 104 at first connector 110. First nasal prong 114 is in fluid communication with first gas supply tube 102 through first connector 110 and nasal cannula body 104. First nasal prong 114 is rotatable in direction 116 around longitudinal axis 112 of nasal cannula body 104 relative to first gas supply tube 102.

While first nasal prong 114 is shown as extending straight up from a surface of nasal cannula body 104, first nasal prong 114 may be curved such that first nasal prong 114 extends into a nare of a patient when nasal cannula 100 is in use. First nasal prong 114 may be oriented on nasal cannula body 104 such that first nasal prong 114 extends into the right nare or the left nare of a patient. First nasal prong 114 on nasal cannula body 104 is rotatable relative to first gas supply tube 102 in direction 116 such that first nasal prong 114 can be rotated within the nare of a patient to achieve a comfortable fit. First nasal prong 114 can also be rotated out of the nare of a patient in order to rest the nare during or between therapy sessions, to allow a patient or health care professional to clean the nare or tissues surrounding the nare, or to administer additional therapies at the nare. Nasal cannula body 104 rotates at first connector 110 to allow the rotation of first nasal prong 114 with respect to first gas supply tube 102. First nasal prong 114 is rotatably adjustable in either rotational direction about longitudinal axis 112 of nasal cannula body 104, such that first nasal prong 114 can be adjusted inward or outward from the face by a user to allow reorientation of first nasal prong 114. Reorientation of first nasal prong 114 may improve the flow of breathing gas within the nasal cavity and decrease irritation to sensitive tissues with more control over directionality of breathing gas flow.

First nasal prong 114 is rotatable with application of sufficient force to effect rotation. Without the application of a deliberate rotational force, first nasal prong 114 remains stationary in position with respect to first gas supply tube 102. The requirement of a deliberate force for rotation of first nasal prong 114 prevents accidental rotational slippage that would alter the orientation of first nasal prong 114 in the nare and potentially diminish effectiveness of the therapy or increase the irritation of tissues if first nasal prong 114 is misaligned due to slipping. First connector 110 and nasal cannula body 104 may be coupled at a junction with adequate material friction to prevent slippage. First connector 110 may be coupled to nasal cannula body 104 by a bearing, which, for example, allows the nasal cannula body 104 to rotate freely about its longitudinal axis 112. In some implementations, the coupling between first connector 110 and nasal cannula body 104 is a journal bearing. In some implementations, the journal bearing has sufficient static frictional torque to maintain the rotational position of first nasal prong 114 relative to first gas supply tube 102. The journal bearing may have a frictional torque of about 0.1 Nm to 1 Nm. In some implementations, the journal bearing has a frictional torque of 0.05 Nm, 0.1 Nm, 0.2 Nm, 0.3 Nm, 0.4 Nm, 0.5 Nm, 0.6 Nm, 0.7 Nm, 0.8 Nm, 0.9 Nm, 1 Nm, 1.2 Nm, 1.5 Nm, 2 Nm, or any other suitable frictional torque. In some implementations, the coupling between first connector 110 and first nasal prong 114 has a surface with contours that allow a series of intermittent rotational stops such that the first nasal prong 114 can be rotated into discreet positions relative to first gas supply tube 102. In some implementations, the coupling between first connector 110 and first nasal prong 114 is barbed. In other implementations, the coupling between first connector 110 and first nasal prong 114 is smooth to allow continuous rotational adjustment of first nasal prong 114 with respect to first gas supply tube 102. In some implementations, nasal cannula body 104 may include a locking mechanism for locking of first nasal prong 114 in a rotational position relative to first gas supply tube 102.

In some implementations, nasal cannula body 104 includes a patient-facing portion (i.e., a section of nasal cannula body 104 that is directly adjacent to a patient) that is fit to a patient anatomy. The patient-fitted portion of nasal cannula body 104 provides stability to the nasal cannula 100 while on the face of a patient. In some embodiments, the patient-fitted portion is a flattened section of plastic or other material fitted to the surface of a patient's face below the nares above the patient's upper lip and incorporating the philtrum. The additional stability of the nasal cannula body 104 increases patient comfort and prevents slippage of the nasal cannula body 104 during use.

In some implementations, first nasal prong 114 is removable from nasal cannula body 104. In such implementations, first nasal prong 114 is manufactured in a variety of sizes, diameters, lengths or angles and can be chosen based on patient anatomy and placed on nasal cannula body 104. A replaceable first nasal prong 114 allows the prong to be chosen to fit the patient and decreases irritation of nasal passages that occurs with ill-fitting or too big nasal prongs. In particular, when nasal cannula 100 is used with HFT systems, ill-fitting nasal prongs may direct heated breathing gas into the nasal tissue and cause irritation or pressure trauma to internal nasal tissues and mucosa during extended use. Rotatably adjustable and replaceable nasal prongs provide flexibility of use and increased patient comfort during use of nasal cannulae.

Figure 2:
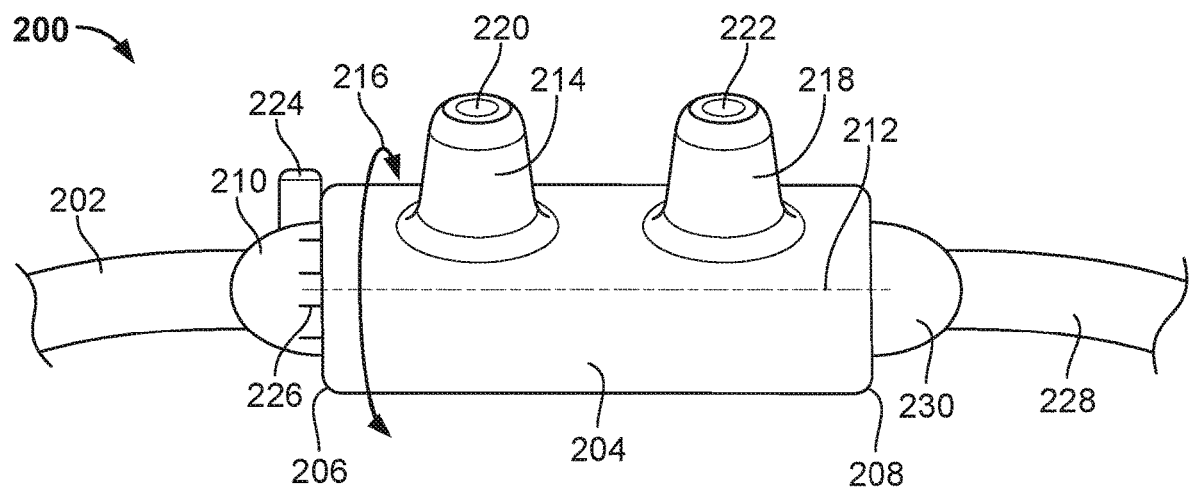
FIG. 2 shows an illustrative nasal cannula with rotatable cannula body.

While FIG. 1 shows a nasal cannula 100 having a single rotatable first nasal prong 114, FIG. 2 shows an illustrative nasal cannula 200 with two prongs and rotatable cannula body. Nasal cannula 200 includes nasal cannula body 204 with first end 206 and second end 208, first nasal prong 214, first outlet 220, second nasal prong 218, second outlet 222, longitudinal axis 212, first gas supply tube 202, first connector 210, second gas supply tube 228, second connector 230, position lock 224, and rotational stop indicators 226. First gas supply tube 202 is connected to first end 206 of nasal cannula body 104 at first connector 210. Second gas supply tube 228 is connected to second end 208 of nasal cannula body 204 at second connector 230. First nasal prong 214 and second nasal prong 218 are in fluid communication with first gas supply tube 202 and second gas supply tube 228, such that a flow of breathing gas through first gas supply tube 202 or second gas supply tube 228 flows through nasal cannula body 104 and out through first outlet 220 and second outlet 222. First nasal prong 214 and second nasal prong 218 are rotatable about longitudinal axis 212 of nasal cannula body 204 with respect to one or both of first gas supply tube 202 and second gas supply tube 228. As in FIG. 1, though first nasal prong 214 and second nasal prong 218 are depicted as extending straight out from a surface of nasal cannula body 204, first nasal prong 214 and second nasal prong 218 may be curved.

First nasal prong 214 and second nasal prong 218 rotate as a unit about longitudinal axis 212 of nasal cannula body 204, allowing the position of first nasal prong 214 and second nasal prong 218 to be adjusted within the nares of a patient. The rotational adjustability of first nasal prong 214 and second nasal prong 218 allows a user to position first nasal prong 214 and second nasal prong 218 such that breathing gas flows through first gas supply tube 202, second gas supply tube 228, and nasal cannula body 204 to exit through first outlet 220 of first nasal prong 214 and second outlet 222 of second nasal prong 218 into the nasal passageway rather than toward sensitive tissues of the nare. The directional adjustment of the breathing gas flow by rotation of first nasal prong 214 and second nasal prong 218 increases efficiency of treatment and increases patient comfort by limiting irritation that can arise from poorly positioned prongs. In particular, during HFT sessions, nasal prongs that are directed toward a sensitive tissue or structure in the nasal cavity can cause pressure trauma to the tissue when heated and pressurized breathing gas is directed at these tissues.

Rotational adjustability of first nasal prong 214 and second nasal prong 218 further allows a user to remove first nasal prong 214 and second nasal prong 218 from the nares in order to clean or rest the nares or to deliver other therapies without removal of the nasal cannula body 204 from the patient's face. Restraining straps (not shown) for first gas supply tube 202 and second gas supply tube 228 that hold the nasal cannula 200 on a patient's face do not need to be removed to allow access to the nares.

First nasal prong 214 and second nasal prong 218 are rotatable about longitudinal axis 212 of nasal cannula body 204 with application of sufficient force to effect rotation, and first nasal prong 214 and second nasal prong 218 remain stationary with respect to first gas supply tube 202 and second gas supply tube 228 in the absence of deliberate rotational force. Thus, first nasal prong 214 and second nasal prong 218 do not slip from position during use. First connector 210 and second connector 230 may be coupled to first end 206 and second end 208 of nasal cannula body 204, respectively, at a junction with adequate material friction to prevent slippage. First connector 210 and second connector 230 may be coupled to nasal cannula body 204 by bearings. In some implementations, the coupling between first connector 210 and nasal cannula body 204, and between second connector 230 and nasal cannula body 204 is a journal bearing. In some implementations, the journal bearing has a frictional torque of about 0.1 Nm to 1 Nm. In some implementations, the journal bearing has a frictional torque of 0.05 Nm, 0.1 Nm, 0.2 Nm, 0.3 Nm, 0.4 Nm, 0.5 Nm, 0.6 Nm, 0.7 Nm, 0.8 Nm, 0.9 Nm, 1 Nm, 1.2 Nm, 1.5 Nm, 2 Nm, or any other suitable frictional torque. In some implementations, one or both of first connector 210 and second connector 230 includes position lock 224 to lock the first nasal prong 214 and second nasal prong 218 in a rotational position relative to first gas supply tube 202 and second gas supply tube 228. In some implementations, one or both of first connector 210 and second connector 230 include contours that allow first nasal prong 214 and second nasal prong 218 to rotate to discreet intermittent rotational positions. In some implementations, one or both of first connector 210 and second connector 230 have smooth surfaces to allow a continuous rotation of first nasal prong 214 and second nasal prong 218 about longitudinal axis 212 of nasal cannula body 204 with respect to first gas supply tube 202 and second gas supply tube 228.

While nasal cannula 200 shows a nasal cannula having a first nasal prong and a second nasal prong, in some embodiments nasal cannula 200 may include a third nasal prong for delivery of aerosolized medicament or other treatment. Third nasal prong (not shown) may be positioned in or on either of first nasal prong 214 or second nasal prong 218. In some implementations, first nasal prong 214 and second nasal prong 218 are in fluid communication with first gas supply tube 202 and first gas supply tube 202 supplies heated and humidified breathing gas to first outlet 220 and second outlet 222 for administration of HFT, while third nasal prong is in fluid communication with second gas supply tube 228, which supplies aerosolized medicament to a third outlet on third nasal prong. In such implementations, third nasal prong is rotatable with first nasal prong 214 and second nasal prong 218 about longitudinal axis 212 of nasal cannula body 204.

Figure 3:
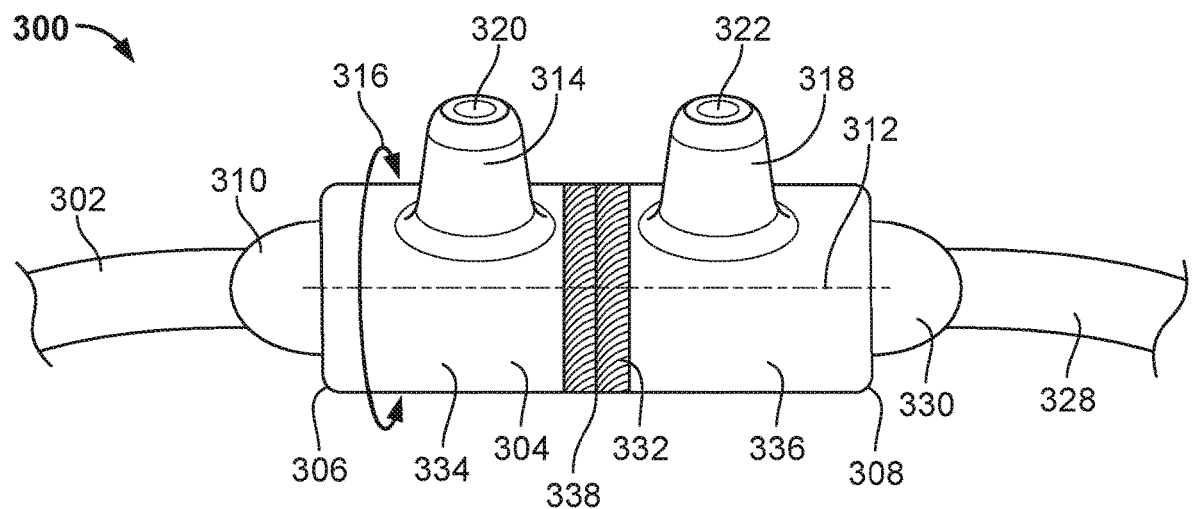
FIG. 3 shows an illustrative nasal cannula with a first section of a cannula body rotatable with respect to a second section.

Nasal cannula 200 of FIG. 2 has two nasal prongs that rotate as a unit about a longitudinal axis of the nasal cannula body. In some implementations, however, a first nasal prong may be rotatable about a longitudinal axis relative to a position of a second nasal prong. FIG. 3 shows an illustrative nasal cannula 300 with a first section 334 of a nasal cannula body 304 rotatable with respect to a second section 336. Nasal cannula 300 includes first gas supply tube 302, first connector 310, second gas supply tube 328, second connector 330, nasal cannula body 304 having first end 306, second end 308, first section 334, second section 336, and longitudinal axis 312, first nasal prong 314, first outlet 320, second nasal prong 318, second outlet 322, separating wall 332, and cannula bearing 338. Nasal cannula body 304 is divided into first section 334, including first nasal prong 314 in fluid communication with first gas supply tube 302, and second section 336, including second nasal prong 318 in fluid communication with second gas supply tube 328. First gas supply tube 302 is coupled to first end 306 of nasal cannula body 304 at first connector 310. Second gas supply tube 328 is coupled to second end 308 of nasal cannula body 304 at second connector 330. First nasal prong 314 and second nasal prong 318 are rotatable in direction 316 about longitudinal axis 312 of nasal cannula body 304 with respect to one or both of first gas supply tube 302 and second gas supply tube 328.

First section 334, including first nasal prong 314, is rotatable about longitudinal axis 312 with respect to a position of second section 336, including second nasal prong 318. In some implementations, first nasal prong 314 and second nasal prong 318 are in fluid communication with each other. First section 334 and second section 336 are joined at cannula bearing 338, allowing independent rotation of first nasal prong 314 on first section 334 and second nasal prong 318 on second section 336. Cannula bearing 338 may be a journal bearing. Independent rotational adjustment of first nasal prong 314 and second nasal prong 318 allows a user to independently position first nasal prong 314 and second nasal prong 318 within the nares of a patient to account for non-symmetrical anatomy of the nasal cavity and structures. Additionally, independent rotational adjustment of first nasal prong 314 and second nasal prong 318 allows a user to rotate first nasal prong 314 out of the nare while leaving second nasal prong 318 directed into the nare so that therapy can continue at one nare while the other nare is rested or cleaned or while additional therapies are administered at the other nare.

In some implementations, first section 334 and second section 336 are not in fluid communication, but rather are divided by separating wall 332. In such implementations, first section 334 and second section 336 are rotatable relative to each other and relative to a position of one or both of first gas supply tube 302 and second gas supply tube 328. Fluid separation of first section 334 and second section 336 allows for administration of different therapies through the first nasal prong 314 and second nasal prong 318. Furthermore, the fluid separation of first section 334 and second section 336 may decrease noise associated with the administration of breathing gas through the nasal cannula 300. Manufacture of first section 334 and second section 336 as separate pieces, which are joined at a separating wall 332, does not require additional seals about the rotatable connection between first section 334 and second section 336.

Figure 4:
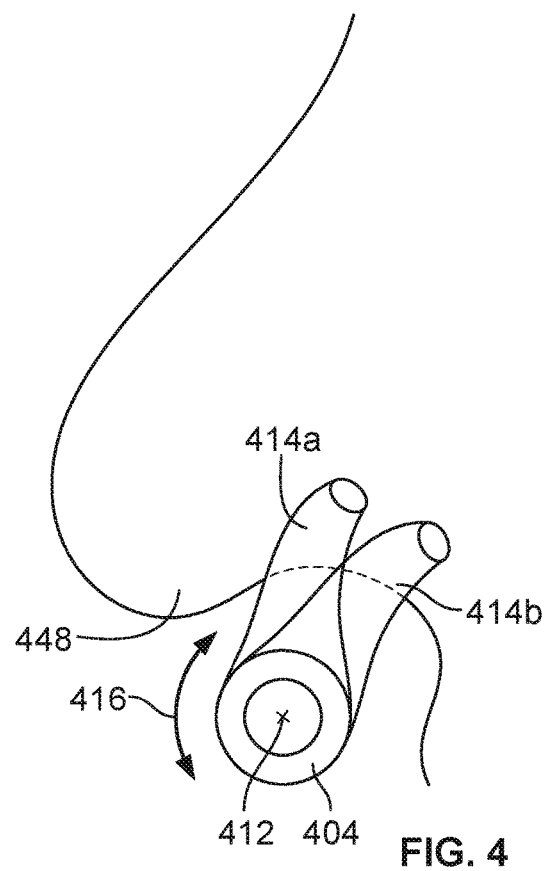
FIG. 4 shows an illustrative cross-sectional view of a nasal cannula with rotatable cannula body section including a nasal prong.

FIG. 4 shows an illustrative cross-sectional view of a nasal cannula, such as nasal cannula 100, 200 or 300 shown in FIG. 1, 2 or 3 having a rotatable nasal prong. The cross-sectional view of the nasal cannula in FIG. 4 shows nasal cannula body 404, first nasal prong 414 situated in patient nare 448. First nasal prong 414 is rotatable in direction 416 about longitudinal axis 412, which may correspond to longitudinal axis 112, of nasal cannula body 404, such that first nasal prong 414 has a first position of first nasal prong 414a having a high entry angle into patient nare 448 and can be rotated into second position of first nasal prong 414b having a shallow entry angle into patient nare 448. Rotational adjustment of first nasal prong 414 allows the position of first nasal prong 414 to be adjusted to fit the nasal cavity anatomy of a patient. In some implementations, first nasal prong 414 is rotated about longitudinal axis in a smooth continuous adjustment. In other implementations, first nasal prong 414 is rotated into discreet positions dictated by contours within a coupling in nasal cannula body 404.

Figure 5:
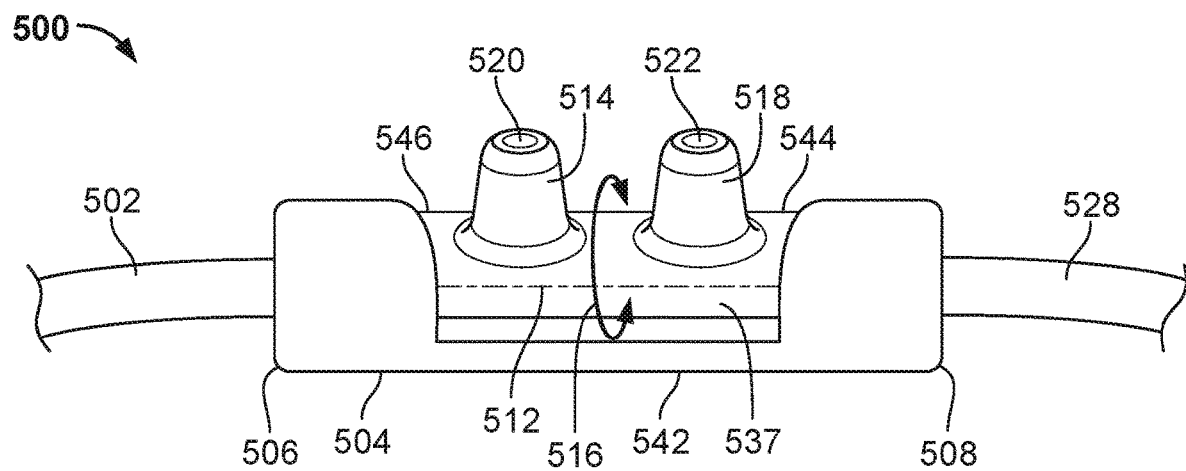
FIG. 5 shows an illustrative nasal cannula with rotatable nasal prongs and a solid bridge section.

In some implementations, a nasal cannula body includes a rotating portion on which nasal prongs are located and a non-rotating portion. FIG. 5 shows an illustrative nasal cannula 500 with rotatable nasal prongs and a solid bridge 542 of the nasal cannula body 504. Nasal cannula 500 includes nasal cannula body 504, first end 506, second end 508, first open end 546, second open end 544, longitudinal axis 512, first gas supply tube 502, second gas supply tube 528, first nasal prong 514, first outlet 520, second nasal prong 518, second outlet 522, and rotating prong element 537. Nasal cannula body 504 includes first end 506 in fluid connection with first open end 546 and second end 508 in fluid communication with second open end 544. First end 506 and second end 508 of nasal cannula body 504 are coupled by solid bridge 542 through which there is no gas flow. Solid bridge 542 may include a patient-facing stabilizing surface that prevents movement of nasal cannula 500 once it is affixed to a patient's face. Rotating prong element 537 includes first nasal prong 514 and second nasal prong 518, and is configured to be inserted into first open end 546 and second open end 544 of nasal cannula body 504. Rotating prong element 537 is rotatable in direction 516 about longitudinal axis 512 with respect to a position of nasal cannula body 504. In some implementations, first end 506 and second end 508 of nasal cannula body 504 are in fluid communication when rotating prong element 537 is inserted into nasal cannula body 504. In some implementations, rotating prong element 537 is removable from nasal cannula body 504.

Rotational adjustment of first nasal prong 514 and second nasal prong 518 on rotating prong element 537 inserted into nasal cannula body 504 allows for adjustment of nasal prong positioning within the nare of a patient while maintaining a stable connection with the patient's face via solid bridge 542 of nasal cannula body 504. Nasal cannula body 504 does not slip or move while first nasal prong 514 and second nasal prong 518 are rotated on rotating prong element 537 to position in the nares or to remove from the nares for cleaning or resting of the nares or for administration of other therapies. The ability to adjust the position of first nasal prong 514 and second nasal prong 518 in a patient's nares without moving the nasal cannula body 504 improves patient comfort by allowing control of breathing gas directionality to protect sensitive tissues. Further, nasal prongs that are adjusted to fit the patient minimizes the need for multiple readjustments of the nasal cannula 500 or first gas supply tube 502 and second gas supply tube 528 during treatment. Movement of gas supply tubes can cause irritation about the ears, and repetitive adjustments during administration of therapies can lead to patient discomfort and development of pressure ulcers. A rotating first nasal prong 514 and second nasal prong 518 on rotating prong element 537 while solid bridge 542 remains in contact with a patient's face for stability decreases the need for readjustment of supply tubes.

In some implementations, nasal cannula 500 is constructed as a quiet nasal cannula in that first nasal prong 514 is in fluid communication with first gas supply tube 502 through first end 506 of nasal cannula body 504 and first open end 546, but first nasal prong 514 is not in fluid communication with second nasal prong 518. In such implementations, first nasal prong 514 and second nasal prong 518 are connected at a separating wall (such as separating wall 332 in FIG. 3), which may be configured as a solid bridge 542 between first nasal prong 514 and second nasal prong 518. The separation of breathing gas flow from first gas supply tube 502 through first outlet 520 from the breathing gas flow from second gas supply tube 528 through second outlet 522 minimizes noise at the nasal cannula body 504 proximal to the patient, because breathing gas flows do not meet between first nasal prong 514 and second nasal prong 518 as when the two prongs are in fluid communication.

Figure 6:
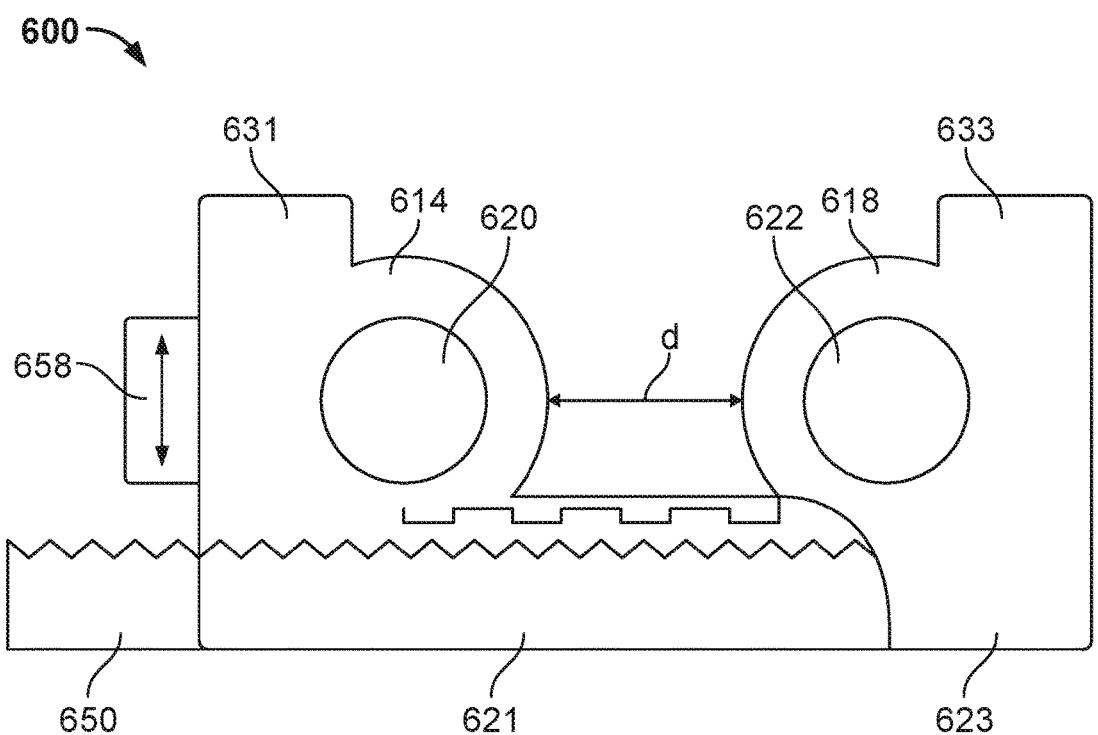
FIG. 6 shows an illustrative nasal cannula allowing adjustment of the distance between prongs.

While nasal cannula 100, 200, 300, and 500 in FIGS. 1, 2, 3, and 5 include rotationally adjustable prongs, in some implementations the distance between prongs can be adjusted. FIG. 6 shows a top view of an illustrative nasal cannula 600 allowing adjustment of the distance between prongs. The mechanism for enabling the adjustment may vary. One mechanism for allowing such adjustment is shown in FIG. 6. Nasal cannula 600 includes first nasal prong 614, second nasal prong 618, first prong assembly 621, second prong assembly 623, first finger tab 631, second finger tab 633, locking teeth 656 and lock 658. First prong assembly 621 includes first nasal prong 614 and first outlet 620. Second prong assembly 623 includes second nasal prong 618, second outlet 622, and an extension comprising locking teeth 656. First prong assembly 621 engages with second prong assembly 623 by accepting the extension, including locking teeth 656, of second prong assembly 623 into an internal track of first prong assembly 621. In some implementations, the internal track of first prong assembly 621 also includes teeth indents to interact with locking teeth 656 and hold first prong assembly 621 and second prong assembly 623 in place. First prong assembly 621 and second prong assembly 623 are held in a position by locking teeth 656 of second prong assembly 623 and lock 658 positioned on first prong assembly 621. The extension comprising locking teeth 656 is toward a patient, and the backside of locking teeth 656 forms a solid face that provides stability against the patient's anatomy beneath the nares. The distance d between first nasal prong 614 and second nasal prong 618 can be changed by pushing first prong assembly 621 and second prong assembly 623 toward each other using first finger tab 631 and second finger tab 633 or by pulling apart.

Nasal cannula 600 can be manufactured in three pieces, comprising first prong assembly 621, second prong assembly 623 and lock 658. Distance d between first nasal prong 614 and second nasal prong 618 can be repeatedly adjusted and distance d is easy to adjust by pulling or pushing on first finger tab 631 and second finger tab 633 on a non-patient facing side of nasal cannula 600. Precise adjustment of distance d between first nasal prong 614 and second nasal prong 618 is possible, allowing for precise placement of first nasal prong 614 and second nasal prong 618 within the nares of a patient for optimal efficiency of treatment and minimal irritation caused by ill-fitting or misaligned prongs.

Figure 7:
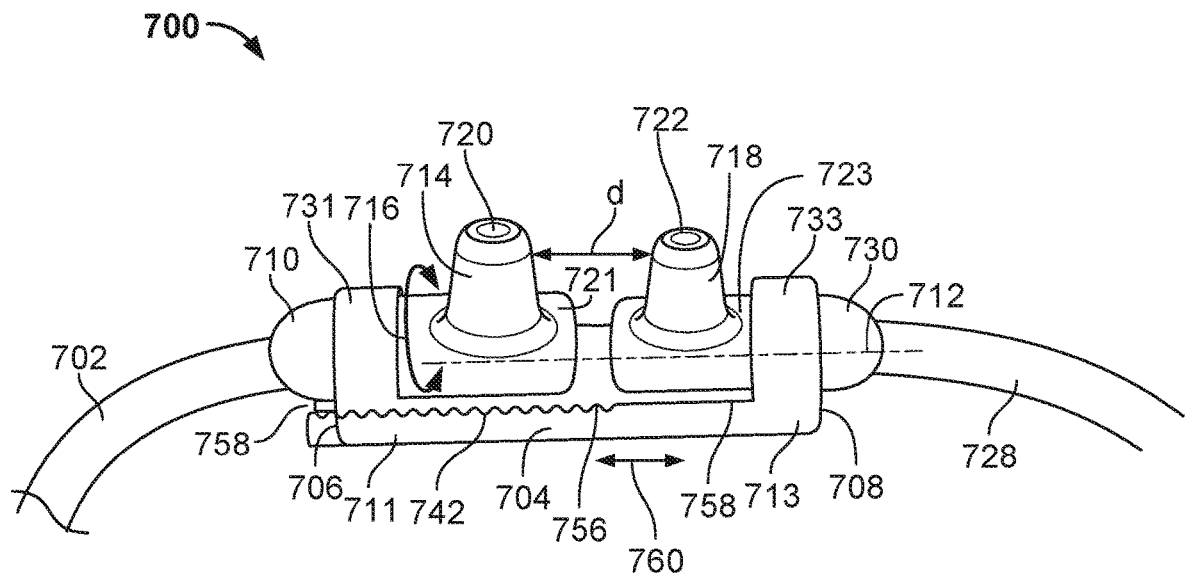
FIG. 7 shows an alternate illustrative nasal cannula allowing adjustment of the distance between nasal prongs.

As shown in FIG. 6 (and FIG. 8 below) nasal cannulas described herein may allow for adjustable distances between prongs. In some implementations, distance between nasal prongs may be adjustable and nasal prongs may also be rotationally adjustable. FIG. 7 shows a nasal cannula 700 allowing adjustment of the distance between nasal prongs as well as rotation of nasal prongs. Nasal cannula 700 includes nasal cannula body 704, consisting of first cannula assembly 711 and second cannula assembly 713, first prong assembly 721, second prong assembly 723, first nasal prong 714, first outlet 720, second nasal prong 718, second outlet 722, first finger tab 731, second finger tab 733, locking teeth 756, lock 758, first gas supply tube 702, first connector 710, second gas supply tube 728 and second connector 730. Nasal cannula body 704 comprises a first end 706 including first cannula assembly 711 and first finger tab 731, and a second end 708, including second cannula assembly 713, second finger tab 733 and an extension including locking teeth 756. First cannula assembly 711 includes a bridge 742 with a hollow passage inside configured to accept the extension of second cannula assembly 713, including locking teeth 756. The hollow passage (not shown) may include notches that interact with locking teeth 756 to hold first cannula assembly 711 and second cannula assembly 713 in position. Locking teeth 756 slide in the hollow passage of bridge 742 to allow first cannula assembly 711 and second cannula assembly 713 to move relative to each other in an axial direction 760 parallel to longitudinal axis 712, changing distance d between first nasal prong 714 on first cannula assembly 711 and second nasal prong 718 on second cannula assembly 713. Lock 758 on second cannula assembly 713 locks the position of first cannula assembly 711 relative to second cannula assembly 713. First gas supply tube 702 is coupled to first end 706 of first cannula assembly 711 at first connector 710 and is also coupled to first prong assembly 721. Second gas supply tube 728 is coupled to second end 708 of second cannula assembly 713 at second connector 730 and is also coupled to second prong assembly 723.

First prong assembly 721 is configured to allow rotation in a direction 716 about longitudinal axis 712. First prong assembly 721 may be coupled to first connector 710 by a bearing, such as a journal bearing allowing continuous or ratcheted rotation. Second prong assembly 723 is configured to allow rotation in direction 716 about longitudinal axis 712. Second prong assembly 723 may be coupled to second connector 730 by a bearing that may be a journal bearing allowing either continuous or intermittent rotation as well. Simultaneous control over rotational adjustment and the distance between first nasal prong 714 and second nasal prong 818 allows a user to precisely adjust the fit of nasal cannula 700 to a particular patient. Precise fitting of the nasal prongs to a patient reduces irritation due to nasal prongs contacting surfaces and tissues within the nares and increases the efficiency of respiratory therapy by directing the flow of breathing gas into the nasal passageway for optimal flushing of the upper respiratory tract. Furthermore, nasal cannula 700 includes first nasal prong 714 and second nasal prong 718 that are not in fluid communication, decreasing the noise associated with breathing gas flows meeting proximal to the patient.

Figure 8:
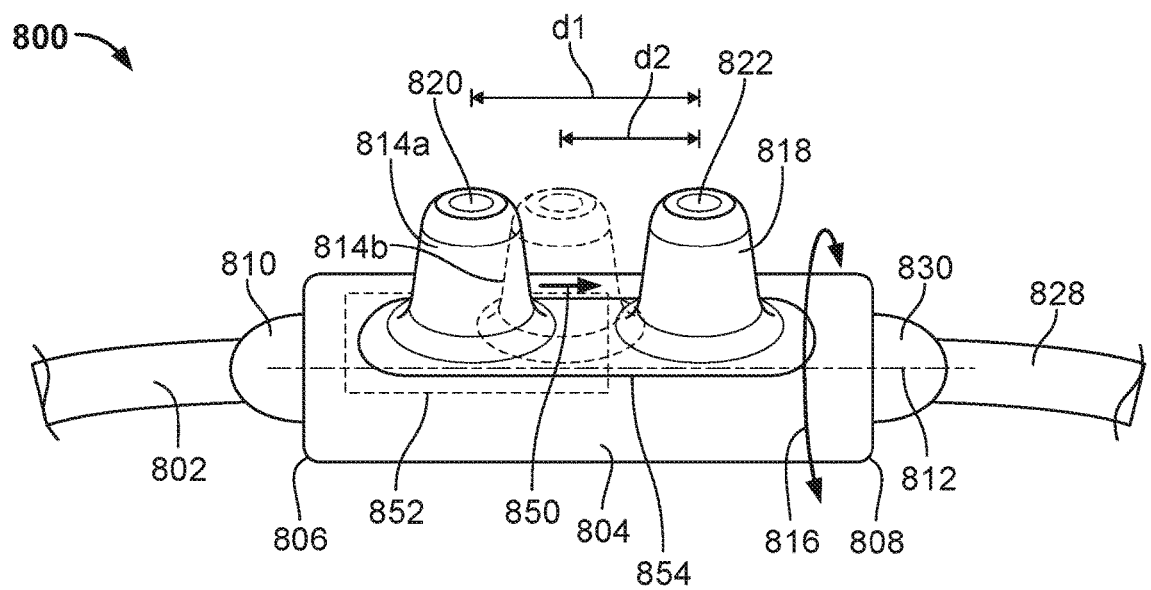
FIG. 8 shows an illustrative nasal cannula allowing adjustment of the distance between nasal prongs and rotation of nasal prongs.

FIG. 8 shows an alternate illustrative nasal cannula 800 allowing adjustment of the distance between nasal prongs and rotation of nasal prongs. Nasal cannula 800 includes nasal cannula body 804, first end 806, second end 808, first gas supply tube 802, first connector 810, second gas supply tube 828, second connector 830, longitudinal axis 812, first nasal prong 814, first outlet 820, second nasal prong 818, second outlet 822, sliding panel 852, and slide track 854. Nasal cannula body 804 is connected at first end 806 to first gas supply tube 802 by first connector 810. Second end 808 of nasal cannula body 804 is coupled to second gas supply tube 828 by second connector 830. Nasal cannula body 804 includes first nasal prong 814 and second nasal prong 818, separated by distance d. Nasal cannula body 804 also includes slide track 854 configured as a cutout in an outer surface of nasal cannula body 804. First nasal prong 814 is positioned on sliding panel 852, which slides in slide track 854 in axial direction 850 parallel to longitudinal axis 812 such that the distance d between first nasal prong 814 and second nasal prong 818 is changeable. For example, first nasal prong 814a on sliding panel 852 with distance d1 from second nasal prong 818 can be moved in axial direction 850 to the position of overlaid first nasal prong 814b having distance d2 from second nasal prong 818. The ability to change the distance d between the first nasal prong 814 and second nasal prong 818 allows the nasal cannula 800 to be fit to the anatomy of patient's of various sizes, increasing patient comfort.

In some implementations, the coupling between the first connector 810 and the first end 806 of the nasal cannula body 804, and the second connector 830 and the second end 808 of the nasal cannula body 804 allow the nasal cannula body 804 to rotate in direction 816 about longitudinal axis 812 with respect to the first gas supply tube 802 and second gas supply tube 828 respectively. This allows the distance between the prongs to be adjusted, as well as rotational adjustments of the position of the prongs within the nare, permitting optimization of the prong orientation in the nares of a patient. As a result, airway flush may be optimized and irritation due to nasal prongs or breathing gas contacting the sensitive tissues in the nare can be lessened.

Figure 9:
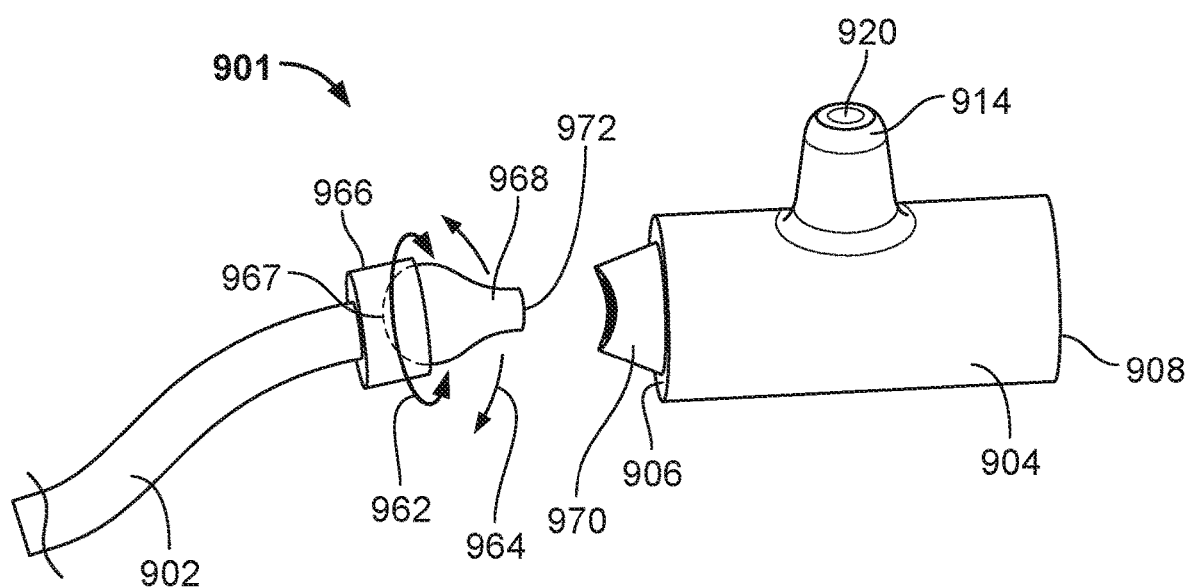
FIG. 9 shows an illustrative swivel connector for coupling to a nasal cannula.

FIG. 9 shows an illustrative swivel connector 901 for coupling a first gas supply tube 902 to a nasal cannula body 904. Swivel connector 901 includes first portion 966 and second portion 968, bearing 967, opening 972, and first gas supply tube 902. Nasal cannula body 904 includes first end 906, second end 908, first nasal prong 914, nozzle opening 972, and adapter 970. First portion 966 of swivel connector 901 is sized to receive first gas supply tube 902. Second portion 968 of swivel connector 901 is coupled to first portion 966 by bearing 967, which allows second portion 968 to rotate within first portion 966. Second portion 968 is able to rotate radially in a radial direction 962 and able to swivel in swivel direction 964. Second portion 968 engages with adapter 970 and first gas supply tube 902 is in fluid communication with nozzle opening 972 through first portion 966 and second portion 968 of swivel connector 901 and through nasal cannula body 904.

The rotational and swivel motions of second portion 968 within first portion 966 allow nasal cannula body 904 to accommodate movement and torque on the first gas supply tube 902 with minimal motion of nasal cannula body. In some implementations, second portion 968 is capable of 360 degree, bidirectional motion. In some implementations, the allowed movement of second portion 968 describes a hemisphere. In some implementations, bearing 967 is incorporated into nasal cannula body 904 rather than on first gas supply tube 902 side. Movement of first gas supply tube 902 between the patient and the breathing gas supply is accommodated by the swivel movement of second portion 968 on bearing 967 such that nasal cannula body 904 is not jostled by movement of first gas supply tube 902. Likewise, movement of nasal cannula body 904 due to a patient talking, moving or eating, for example, does not translate to motion of first gas supply tube 902. Minimization of movement of first gas supply tube 902 decreases the occurrence of patient injury and irritation due to rubbing of the first gas supply tube 902 on patient skin. In particular, when first gas supply tube 902 is used for delivery of heated and humidified breathing gas for HFT, minimization of rubbing is critical to patient comfort as heated and pressurized supply tubes may cause pressure ulcers where they rub on a patient's skin.

Figure 10:
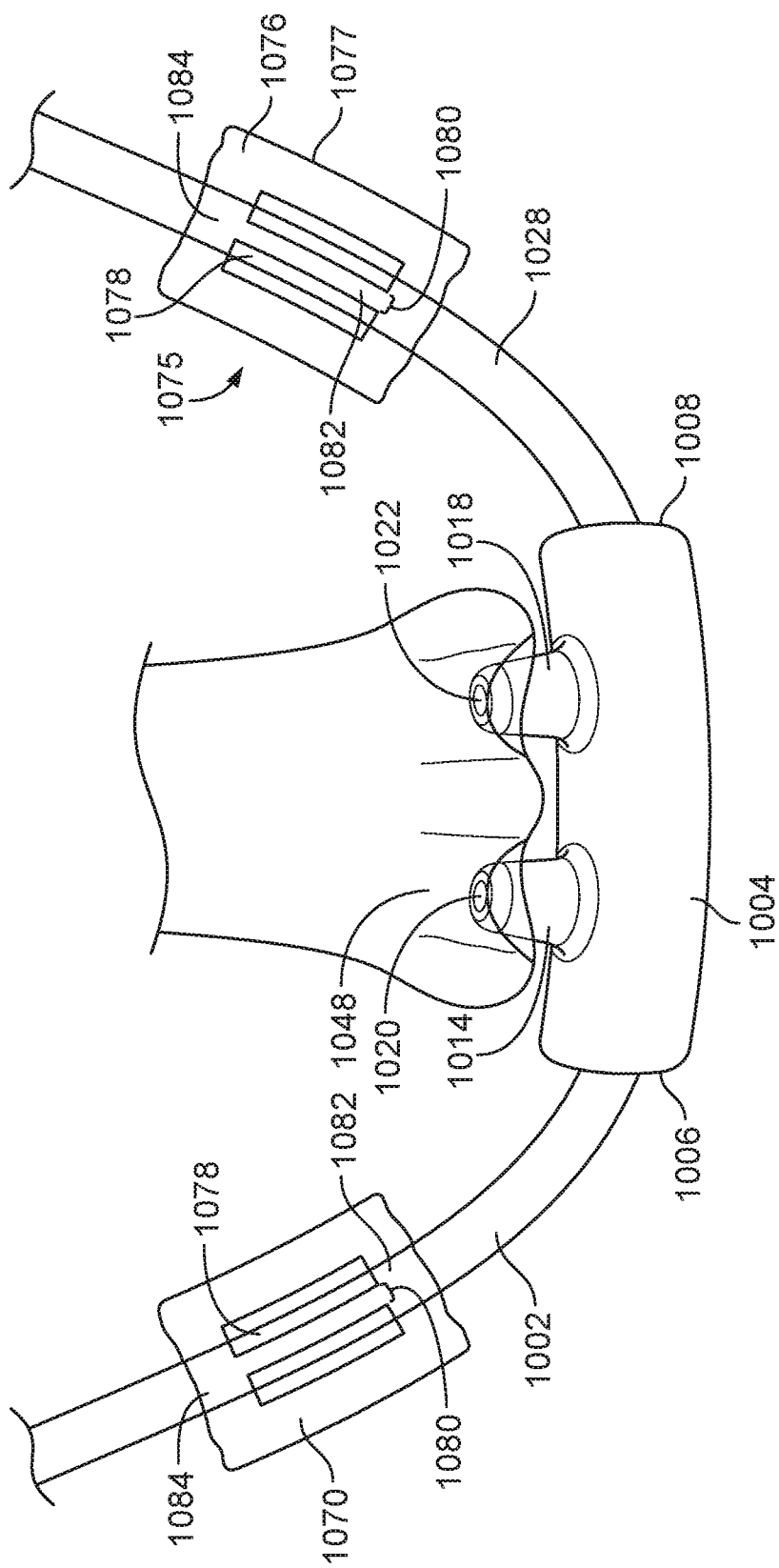
FIG. 10 shows an illustrative tubing guide for use with gas supply tubing of a nasal cannula.
Figure 11:
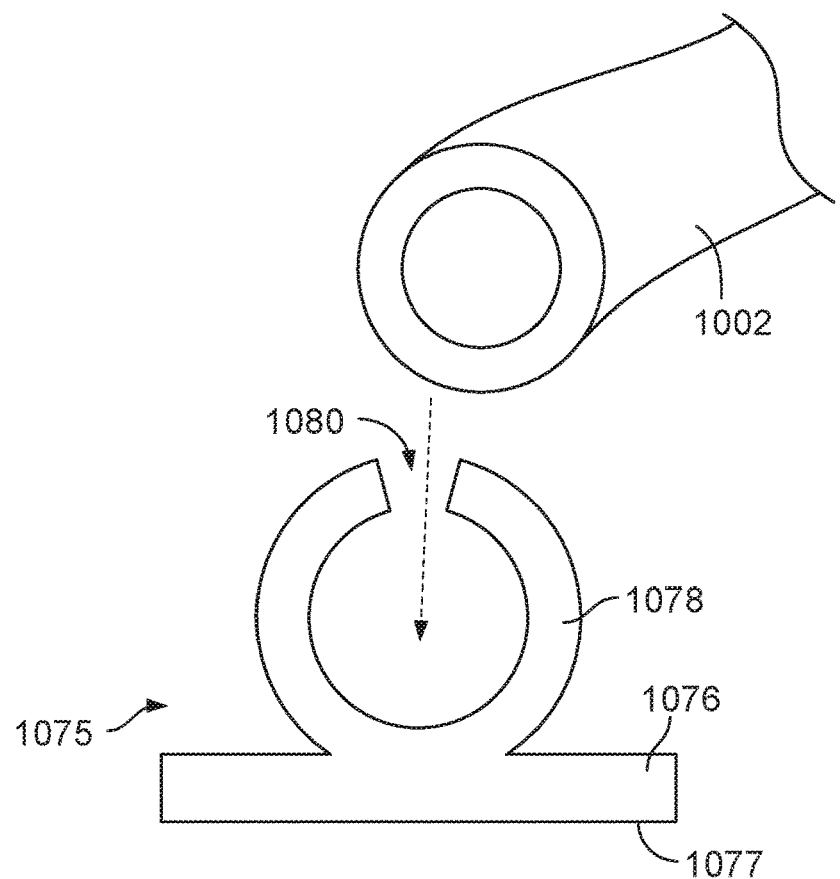
FIG. 11 shows an illustrative cross-sectional view of a tubing guide for use with gas supply tubing of a nasal cannula.

FIG. 10 shows an illustrative tubing guide fastener 1075 for use with first gas supply tube 1002 of a nasal cannula body 1004. FIG. 11 shows a cross-sectional view of tubing guide fastener 1075. Tubing guide includes flexible body 1076, guide connector 1078, slit 1080, first end opening 1082, second end opening 1084, and adhesive bottom 1077. Flexible body 1076 is configured to be flat with adhesive bottom 1077 on a patient-facing side. Guide connector 1078 is configured as a circular or tube-shaped feature positioned across flexible body 1076 with slit 1080 running from first end opening 1082 to second end opening 1084 of guide connector 1078 permitting introduction of first gas supply tube 1002. Guide connector 1078 is sized to accept first gas supply tube 1002, which can be pressed through slit 1080 into guide connector 1078 where first gas supply tube 1002 is held in position. Flow of breathing gas through first gas supply tube 1002 is not impaired by guide connector 1078, and gas supply tube is in fluid communication with nasal cannula body 1004. Adhesive bottom 1077 is configured to releasably adhere to skin of a patient.

Tubing guide fastener 1075 is configured to hold a first gas supply tube 1002 in a position on a patient, for example, on a patient's cheek, to ensure that first nasal prong 1014 remains in an optimized position within nare 1048. In some implementations, two tubing guide fasteners 1075 may be used to affix gas supply tubes to each of a patient's cheek. In some implementations, guide connector 1078 may be sized for small-bore tubing (e.g., NG tubing, IV tubing, umbilical catheters) or wide-bore patient tubing. In some implementations, guide connector 1078 runs straight across flexible body 1076. In other implementations, guide connector 1078 is curved across the surface of flexible body 1076. In some implementations, guide connector 1078 forms almost a complete circular cross-section. In some implementations, guide connector 1078 is sticky on an interior surface or otherwise grips first gas supply tube 1002 to avoid inadvertent movement of first gas supply tube 1002. In other implementations, guide connector 1078 is able to slide along and/or rotate around first gas supply tube 1002.

In some implementations, flexible body 1076 may be constructed from a single piece of plastic or silicone. In some implementations, adhesive bottom 1077 comprises a small hydrogel hydro-colloidal adhesive. Adhesive bottom 1077 is biocompatible and removable with minimal irritation or residue. In some implementations, tubing guide fastener 1075 is configured for use on a patient's cheek, nose or any other facial geometry. Tubing guide fastener 1075 not only provides a mechanism for affixation of first gas supply tube 1002 to the skin, but also allows a user to orient first gas supply tube for optimal placement of first nasal prong 1014 in nare 1048. Slit 1080 permits introduction and removal of first gas supply tube 1002, and, upon reintroduction of first gas supply tube 1002 to slit 1080 in guide connector 1078, first gas supply tube 1002 is immediately returned to proper orientation. Tubing guide fastener 1075 may be used with any respiratory therapy. Tubing guide fastener 1075 may be particularly useful for retaining gas supply tubing used for delivery of HFT, because correct positioning of nasal prongs in the nares is important to provide optimum flushing of the upper respiratory tract.

Figure 12:
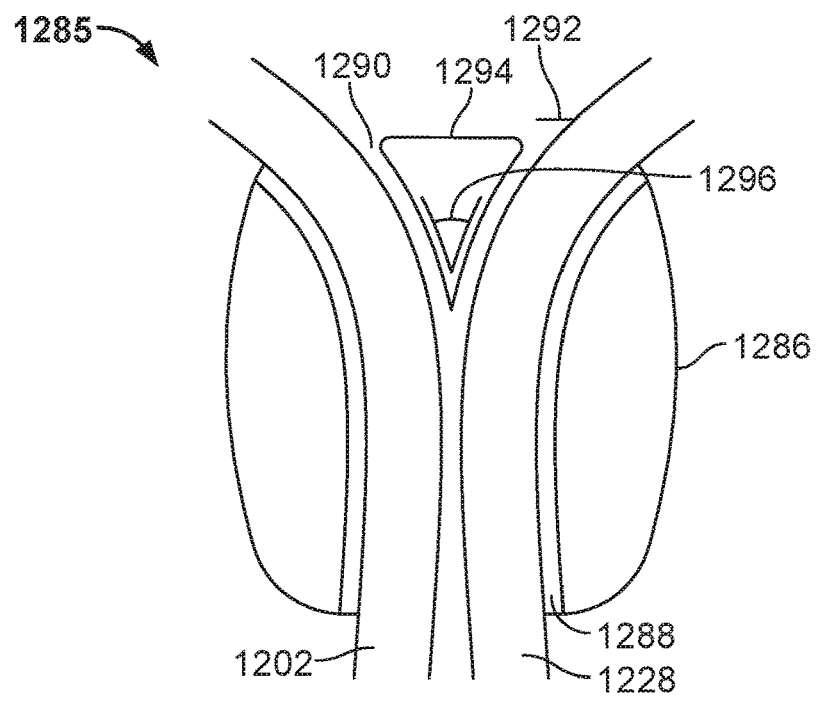
FIG. 12 shows an illustrative view of a slidable connector for use with gas supply tubing of a nasal cannula.

FIG. 12 shows an illustrative view of a slidable connector 1285 for use with gas supply tubing of a nasal cannula. Slidable connector 1285 includes body 1286, first opening 1288, second opening 1290, third opening 1292, and wedge 1294. First opening 1288 is sized to receive first gas supply tube 1202 and second gas supply tube 1228. Second opening 1290 is sized to receive first gas supply tube 1202. Third opening 1292 is sized to receive second gas supply tube. A passageway is formed through body 1286 from first opening 1288 to second opening 1290 in which first gas supply tube 1202 passes. A passageway is formed through body 1286 from first opening 1288 to third opening 1292 through which second gas supply tube 1228 passes. Second opening 1290 and third opening 1292 are separated by wedge 1294. First gas supply tube 1214 and second gas supply tube 1218 diverge about wedge 1294. Wedge 1294 dictates angle 1296 at which first gas supply tube 1202 and second gas supply tube 1228 exit from body 1286.

Slidable connector 1285 retains first gas supply tube 1202 and second gas supply tube 1228 and is slidable along first gas supply tube 1202 and second gas supply tube 1228 in order to temporarily shorten or lengthen a look of gas supply tubing around a patient's ears for securing the nasal cannula to the patient's face. The angle 1296 at which first gas supply tube 1202 and second gas supply tube 1228 exit slidable connector 1285 prevents kinking of first gas supply tube 1202 and second gas supply tube 1228 at the edge of body 1286. Because kinking is prevented, outflow of gas to the patient through first gas supply tube 1202 and second gas supply tube 1228 is continuous and is not interrupted. Kinking changes the flow characteristic of the gas and can increase noise level in the outflow of gas as it exits the nasal prong. In some implementations, slidable connector 1285 includes guide paths for first gas supply tube 1202 and second gas supply tube 1228. In other implementations, it is not necessary to include guide paths within body 1286.

In some implementations, the interior of slidable connector 1285 serves to grip an exterior of first gas supply tube 1202 and second gas supply tube 1228 to maintain persistent sizing of the slidable connector 1285 without slippage such that first gas supply tube 1202 and second gas supply tube 1228 are held in position in slidable connector 1285 until a force is applied to slidable connector 1285 to move slidable connector 1285 along first gas supply tube 1202 and second gas supply tube 1228. In some implementations, first gas supply tube 1202 and second gas supply tube 1228 are parallel to each other at first opening 1288 and are guided in curved paths away from each other to second opening 1290 and third opening 1292, respectively. The curved path prevents the skin from being wedged between the tubing and the slidable connector 1285. In some implementations, an end of body 1286 moves toward wedge 1294 which is patient-facing includes a material to improve comfort or reduce slippage on the skin. For example, the end of body 1286 may be formed of plastic or may be cushioned. A cushioned end of body 1286 may serve to protect skin of a patient from rubbing on heated and pressurized tubing during administration of HFT and may prevent irritation, as well as kinking of first gas supply tube 1202 and second gas supply tube 1228. In some implementations, an end of body 1286 moves toward wedge 1294 which is patient-facing includes a stand-off portion (not shown) which is raised to contact a chin of the patient to further decrease occurrence of kinking of first gas supply tube 1202 and second gas supply tube 1228 for continuous delivery of breathing gas.

Figure 13:
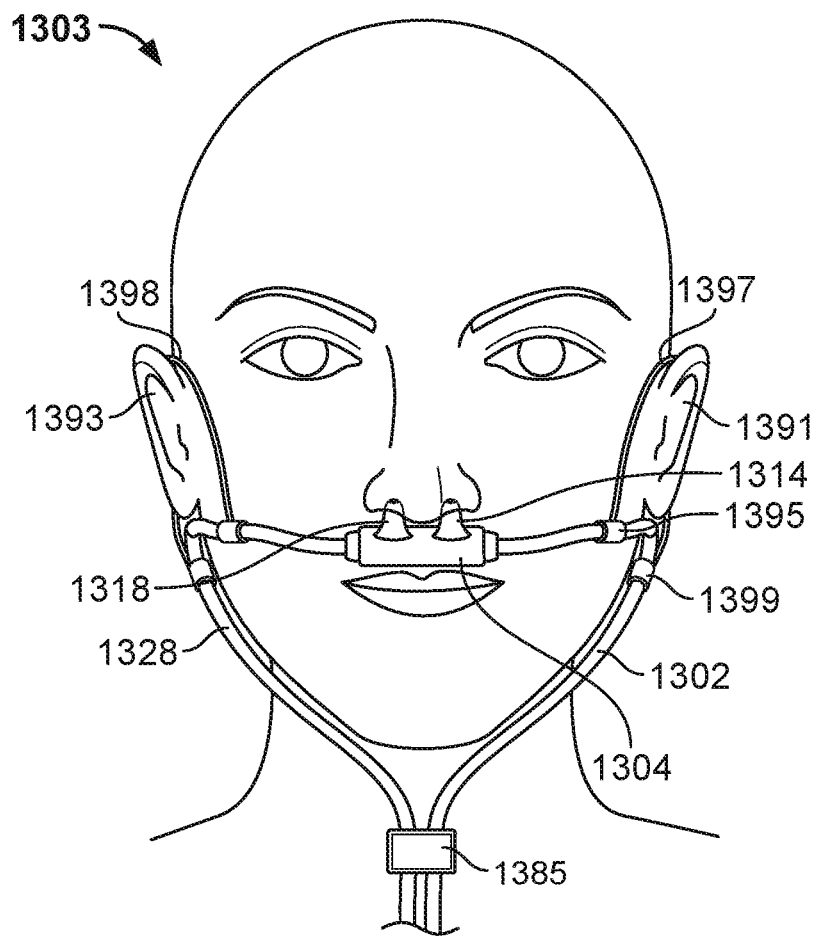
FIG. 13 shows an illustrative view of a fastening mechanism for use with gas supply tubing of a nasal cannula.
Figure 14:
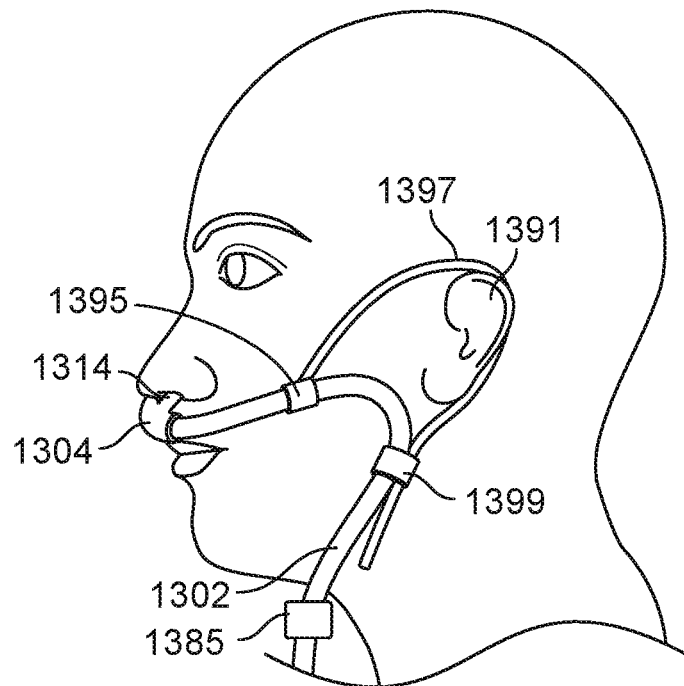
FIG. 14 shows an alternative illustrative side-view of the fastening mechanism for use with gas supply tubing of a nasal cannula.

FIG. 13 shows an illustrative view of a fastening mechanism 1303 for use with first gas supply tube 1302 of a nasal cannula having first over ear connector 1397 and second over ear connector 1398 to decrease the incidence of pain associated with gas supply tubing around the ears. FIG. 14 shows a side-view of the fastening mechanism 1303. Fastening mechanism 1303 includes first gas supply tube 1302, second gas supply tube 1328, nasal cannula body 1304, first over ear connector 1397, second over ear connector 1398, first tube sliding connector 1395 and second tube sliding connector 1399. First gas supply tube 1302 and second gas supply tube 1328 are fluidically coupled to nasal cannula body 1304 to provide breathing gas to first nasal prong 1314 and second nasal prong 1318. First gas supply tube 1302 and second gas supply tube 1328 are affixed to the patient's face by first over ear connector 1397 and second over ear connector 1398, respectively. First gas supply tube 1302 is connected to first over ear connector 1397 at first tube sliding connector 1395 and second tube sliding connector 1399 at a bottom of first ear 1391. First over ear connector 1397 is configured to be placed over a first ear 1391 of a patient and is affixed to first gas supply tube 1302 at first tube sliding connector 1395 and second tube sliding connector 1399 such that first gas supply tube 1302 is suspended from first over ear connector 1397 looped over first ear 1391. First tube sliding connector 1395 and second tube sliding connector 1399 are configured to be slidable over first gas supply tube 1302 to adjust the orientation of first gas supply tube 1302. In some implementations, first tube sliding connector 1395 and second tube sliding connector 1399 are configured as friction fit barrels which allow a length to be adjusted by pulling an end of first over ear connector 1397 through second tube sliding connector 1399. A length of first over ear connector 1397 can be adjusted multiple times using second tube sliding connector 1399, and fastening mechanism 1303 can be precisely fit to a facial geometry such that first nasal prong 1314 and second nasal prong 1318 are properly positioned on a patient's face. In some implementations, first over ear connector 1397 is elastomeric.

First over ear connector 1397 and second over ear connector 1398 serve to affix nasal cannula body 1304 and first gas supply tube 1302 and second gas supply tube 1328 to a patient's face without first gas supply tube 1302 and second gas supply tube 1328 contacting the ears. Suspending first gas supply tube 1302 and second gas supply tube 1328 from the ears without allowing first gas supply tube 1302 and second gas supply tube 1328 to touch the sensitive skin around the ears serves to affix nasal cannula body 1304 to the face without irritating the skin around the ears with hot and pressurized tubing. The shorter path length which breathing gas, and, in particular, heated and humidified breathing gas for HFT, must travel through first gas supply tube 1302 prevents condensation of the gas in the supply tube known as "rainout." Furthermore, the over the ear suspension of fastening mechanism 1303 allows a patient to eat or drink unencumbered while wearing nasal cannula body 1304 and fastening mechanism 1303. In some implementations, a fabric encasement covers a portion of first over ear connector 1397 at the top of first ear 1391 to further protect the skin around the ear from irritation from the tubing. The fabric encasement may be a wicking fabric or a low-friction fabric. In some implementations, a wire structure surrounds all or a portion of first over ear connector 1397 at the top of first ear 1391 to hold first over ear connector 1397 further away from first ear 1391. In some implementations, the wire structure instead comprises a skeleton of pliable plastic plates or a foam cushion layer. The wire structure may be encased within the fabric encasement. In other implementations, the fabric encasement may be comprised of silicone to reduce movement of first over ear connector 1397 on the skin. In some implementations, the silicone encasement comprises a silicone sheet which curls around first over ear connector 1397. The silicone encasement may comprise two silicone sheets joined by silicone adhesive which can be used to label first over ear connector 1397 or may be used to encase first gas supply tube 1302 to provide a more comfortable surface where the skin and first gas supply tube 1302 meet. Fastening mechanism 1303 may be used on its own with any respiratory therapy that requires affixation of gas supply tubes to a patient's face. Fastening mechanism 1303 may be used with other features for retaining gas supply tubes, such as with slidable connector 1385. Fastening mechanism 1303 may be used with HFT systems to prevent irritation to skin caused by rubbing of wide-bore gas supply tubes on and around the ears by suspending the gas supply tubes below the ears with over ear loops.

In some implementations, first over ear connector 1397 and second over ear connector 1398 are configured for use with small-bore gas supply tubing. In other implementations, first over ear connector 1397 and second over ear connector 1398 are configured for use with wide-bore gas supply tubing. In some implementations, first gas supply tube 1302 is a dual-lumen supply tube. In some implementations, first gas supply tube 1302 comprises a first lumen through which breathing gas passes, and a second lumen surrounding the first lumen through which cooled gas passes. In some implementations, the second lumen has micro-pores allowing the cooled gas to flow out of the second lumen to create an air buffer of cooled gas between a patient's skin and the gas supply tube. In some implementations, the cannula is also constructed to have a separate flow path about the outside of the cannula through which cooled gas passes, the separate flow path including micro-pores through which the cooled gas flows towards the patient's skin. The air buffer created between the tubing and/or cannula and the patient's skin lessens the pressure exerted by the tubing on the skin and decreases rubbing on the skin leading to less skin breakdown.

Figure 15:
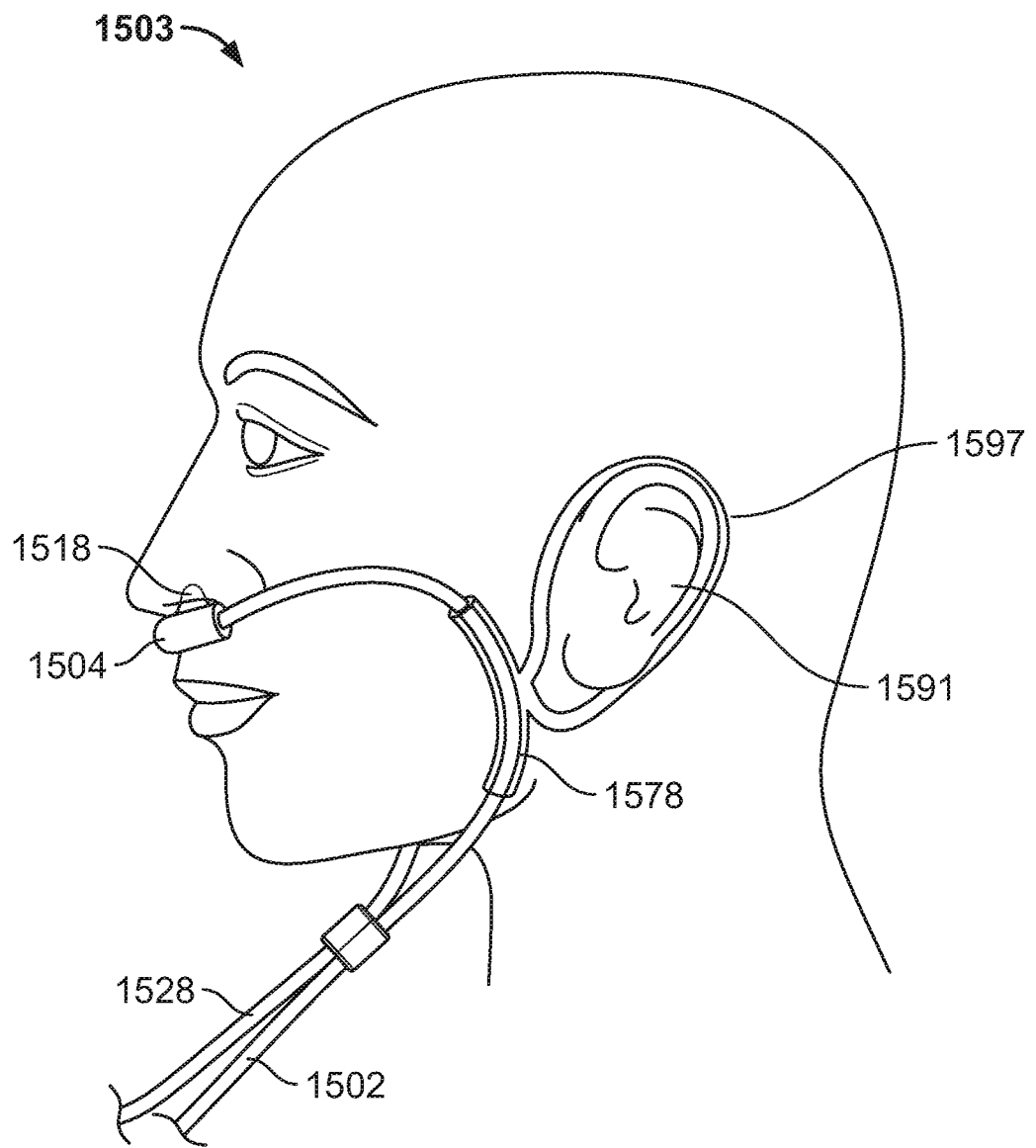
FIG. 15 shows an illustrative view of an alternative fastening mechanism having ear loops.

While FIGS. 13 and 14 show a fastening mechanism 1303 making use of over ear connectors which support gas supply tubes hanging below the ears, FIG. 15 shows an alternative fastening mechanism 1503 in which full ear loops suspend gas supply tubes below the ears. Fastening mechanism 1503 includes first over ear connector 1597, guide connector 1578, and first gas supply tube 1502 connected to nasal cannula body 1504. First over ear connector 1597 is configured as a full loop shaped to hang over and around a first ear 1591 of a patient. First over ear connector 1597 is coupled at a bottom point, configured to be at the bottom of the ear, to first tube guide connector 1578. Guide connector 1578 has a similar shape as guide connector 1078 in FIG. 10 such that guide connector is configured as a column having openings at either end sized to fit first gas supply tube 1502 and having a slit between the openings such that first gas supply tube 1502 can be inserted into guide connector 1578 and held in place. Guide connector 1578 may be coupled to first over ear connector 1597 at an angle such that when first gas supply tube 1502 is inserted into guide connector 1578 it is held in a particular orientation on a patient's face. First gas supply tube 1502 is inserted into guide connector 1578 and is supported by first over ear connector 1597 on first ear 1591. First gas supply tube 1502 supplies gas to nasal cannula body 1504 and through first nasal prong 1518 to a patient's nare. First gas supply tube 1502 is held in a position such that first nasal prong 1518 is appropriately oriented in a patient's nare to provide continuous and effective respiratory therapy.

Although only first gas supply tube 1502 is shown in fastening mechanism 1503, second gas supply tube 1528 is supported by a similar over ear loop over the second ear (not shown). Supporting the first gas supply tube 1502 and second gas supply tube 1528 with over ear connectors such that the first gas supply tube 1502 and second gas supply tube 1528 pass under the ear prevents chafing and irritation of the sensitive tissue about the ears. During use, the first gas supply tube 1502 and second gas supply tube 1528 may rub or become warm, particularly when used with HFT, which can cause discomfort and lead to development of MDRPUs with extended use. Supporting and orienting the first gas supply tube 1502 and second gas supply tube 1528 on the patient's face without placing the first gas supply tube 1502 and second gas supply tube 1528 over the ears prevents discomfort and irritation while affixing the gas supply tubing and nasal cannula to a patient.

In some implementations, guide connector 1578 is sized to fit small-bore tubing. In other implementations, guide connector 1578 is sized to fit wide-bore tubing or any other size of medical tubing. In some implementations, first over ear connector 1597 is produced in different sizes to fit a variety of patient ears. In some implementations, first over ear connector 1597 is flexible or elastically stretchable in order to fit a variety of shapes and sizes of ears. In some implementations, first over ear connector 1597 and guide connector 1578 are separate pieces which may be individually selected and coupled together in order to fit a patient. In some implementations, additional cushions, padding, or fabric encasement is used in conjunction with first over ear connector 1597 to provide additional comfort to the patient.

Figure 16:
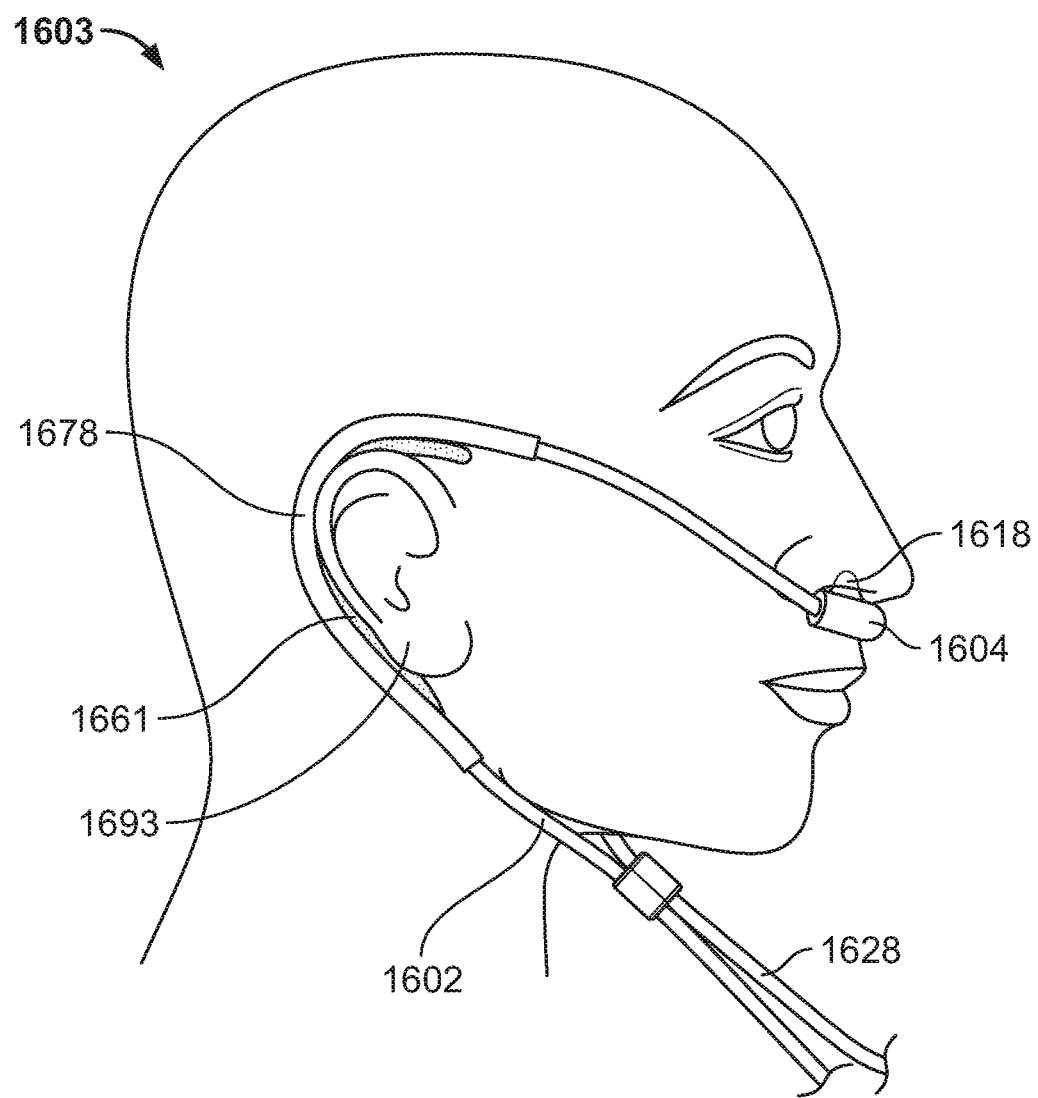
FIG. 16 shows an illustrative view of a fluid filled cushion for use with gas supply tubing of a nasal cannula.

While FIGS. 13-15 show fastening mechanisms in which the gas supply tube passes under the ear, FIG. 16 shows an illustrative view of a fastening mechanism 1603 using a fluid filled cushion 1661 to allow the first gas supply tube 1602 to pass over and around first ear 1691 without causing patient discomfort. Fastening mechanism 1603 includes fluid filled cushion 1661, guide connector 1678, first gas supply tube 1602, and nasal cannula body 1604. Fluid filled cushion 1661 rests against first ear 1691 between first ear 1691 and first gas supply tube 1602 in guide connector 1678. Fluid filled cushion 1661 prevents first gas supply tube 1602 from contacting the sensitive skin surrounding first ear 1691. Fluid filled cushion 1661 protects the skin around first ear 1691 from rubbing on the plastic gas supply tubing and from heat that may accompany the flow of gas through first gas supply tube 1602. Fluid filled cushion 1661 is coupled to guide connector 1678. Guide connector 1678 is configured as a split tube sized to fasten to first gas supply tube 1602 to hold first gas supply tube 1602 in place over first ear 1691.

Fluid filled cushion 1661 may be a pre-filled balloon or foam cushion which acts as an air cushion over first ear 1691. Fluid filled cushion 1661 may collapse slightly behind first ear 1691 to help secure first gas supply tube 1602 and nasal cannula body 1604 in place such that first nasal prong 1618 is properly positioned in the nare. Slightly collapsed fluid filled cushion 1661 may prevent slipping and rubbing about and behind the ear. In some implementations, fluid filled cushion 1661 completely surrounds the ear. In other implementations, fluid filled cushion 1661 is long enough to cover a top of the ear or a top and back portion of the ear. In some implementations, fluid filled cushion 1661 is about 3 to 8 inches in length. In some implementations, fluid filled cushion 1661 is used without guide connector 1678 and first gas supply tube 1602 rests directly on fluid filled cushion 1661 over first ear 1691.

Figure 17:
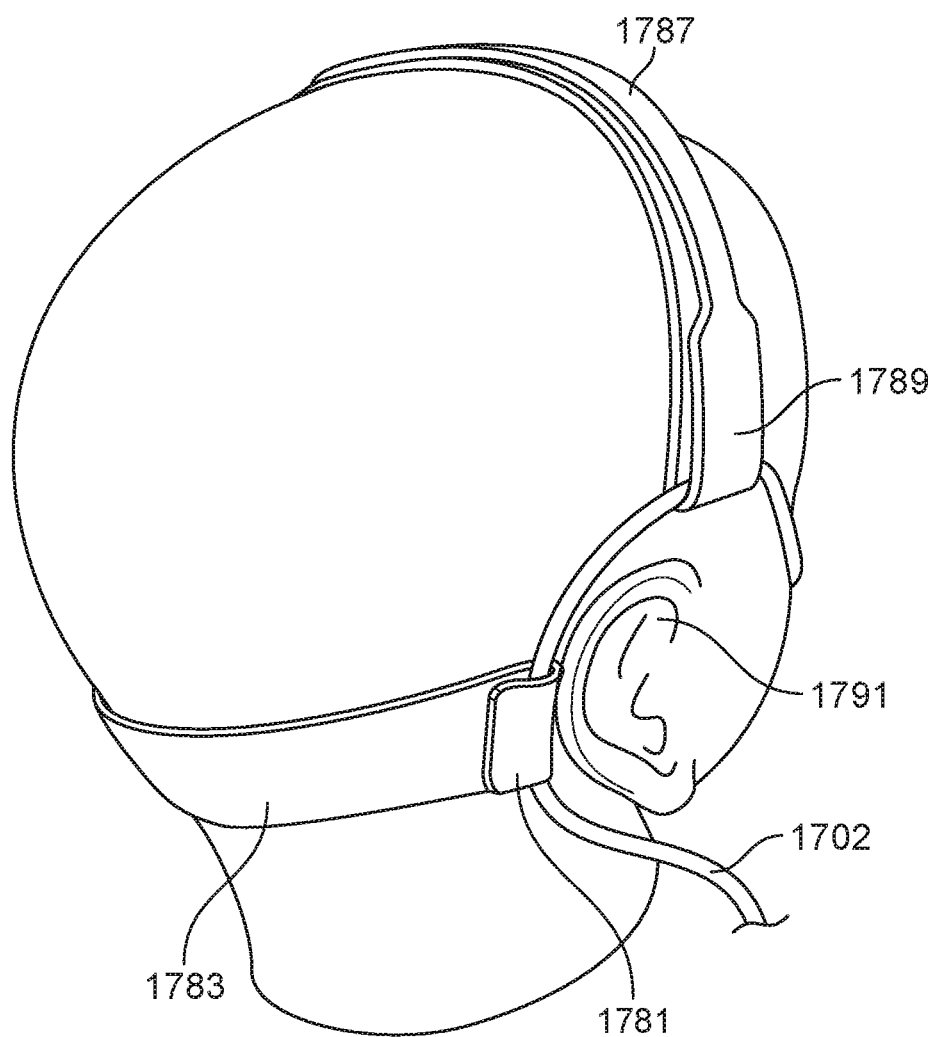
FIG. 17 shows an illustrative view of head straps for use with gas supply tubing of a nasal cannula.

FIG. 17 shows an illustrative view of first head strap 1783 and second head strap 1787 for use with gas supply tubing of a nasal cannula. First head strap 1783 has a first strap closure 1781. Second head strap 1787 has a second strap closure 1789. First head strap 1783 is configured to extend from behind a first ear 1791 along the nape of the neck just below the occipital curvature at the posterior-inferior portion of the head to a second ear (not shown). First strap closure 1781 at an end of first head strap 1783 is configured to retain first gas supply tube 1702 behind first ear 1791 without contacting first ear 1791. Second head strap 1787 is configured to extend sagittally from first ear 1791 across a top of the head to the second ear (not shown). Second strap closure 1789 at an end of second head strap 1787 is configured to retain first gas supply tube 1702 above first ear 1791 without contacting first ear 1791 such that first gas supply tube 1702 is suspended above and behind first ear 1791 without contacting first ear 1791. First head strap 1783 and second head strap 1787 are configured to also hold a second gas supply tube (not shown) above and behind a second ear in the same fashion. Suspending gas supply tubes above the ears of a patient prevents irritation around the patient's ears due to heat and pressure from the gas supply tube.

First strap closure 1781 and second strap closure 1789 may be Velcro, tape or any other clasping mechanism which encloses first gas supply tube 1702. In some implementations, first strap closure 1781 and second strap closure 1789 are composed of stretchable material such as a fabric, polyurethane, rubber or neoprene, or any other suitable material. In some implementations, only first head strap 1783 is required. In some implementations, additional head straps may be required. First head strap 1783 and second head strap 1787 may be used alone or in combination with other fastening devices, such as those disclosed herein.

Figure 18:
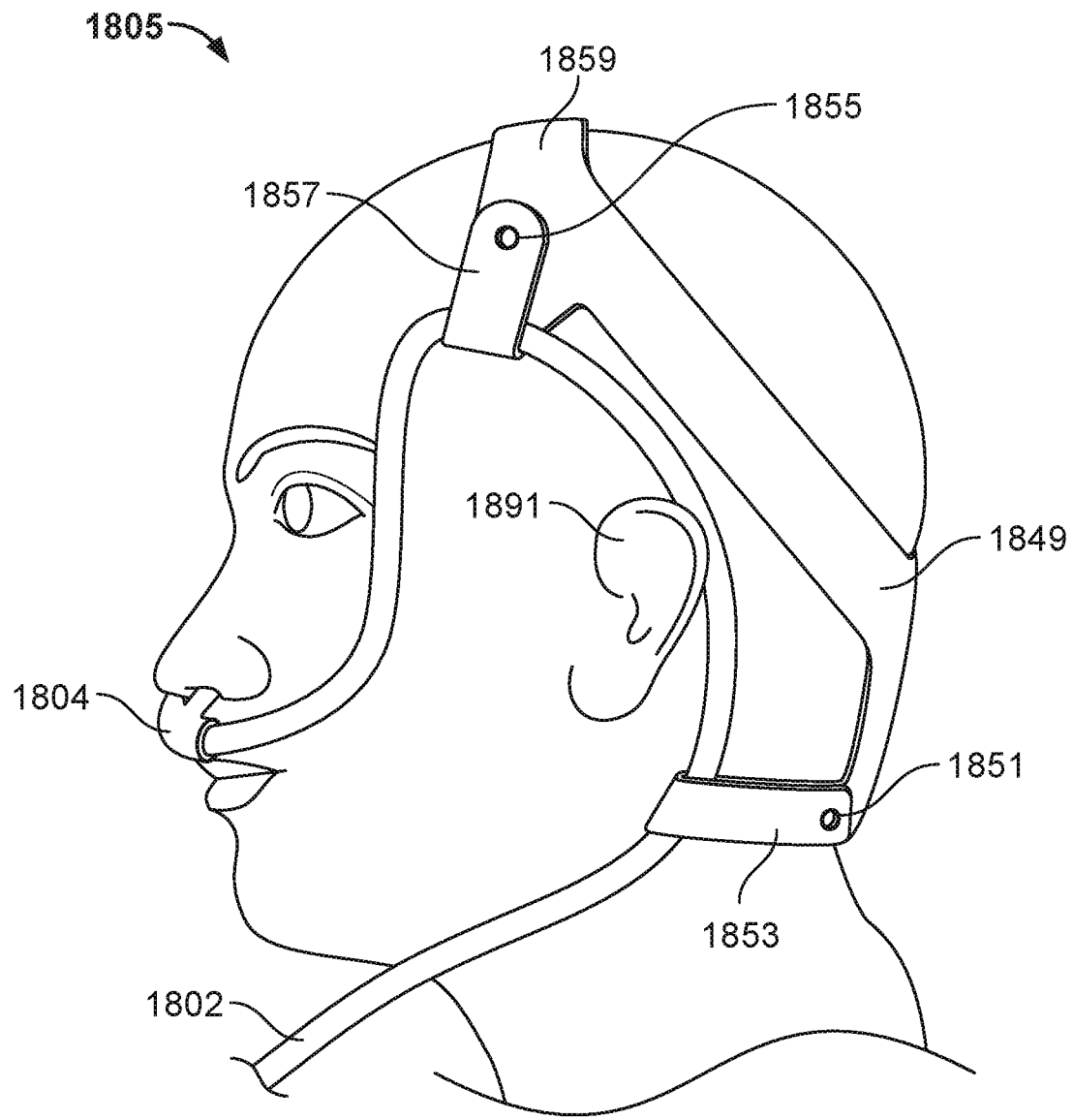
FIG. 18 shows an illustrative view of a strap system for use with a gas supply tubing of a nasal cannula.

FIG. 18 shows an illustrative view of a fastening mechanism 1803 configured as a strap system for use with a gas supply tubing of a nasal cannula. Fastening mechanism 1803 includes sagittal head strap 1859, sagittal strap arm 1857, sagittal strap clasp 1855, occipital head strap 1851, occipital strap arm 1853, occipital strap clasp 1858, and halo connecting strap 1849. Sagittal head strap 1859 is configured to extend sagittally over a top portion of a patient's head. Sagittal strap arm 1857 is configured to loop under first gas supply tube 1802 and double back over itself to retain first gas supply tube 1802 above first ear 1891. Sagittal strap arm 1857 is held in place by sagittal strap clasp 1855. Occipital head strap 1851 is configured to extend about a patient's head in the posterior inferior region of the head, near or below the occipital bone. Occipital strap arm 1853 at an end of occipital head strap 1851 is configured to extend under first gas supply tube 1802 a double back over itself to be clasped in place by occipital strap clasp 1858. Occipital strap arm 1853 retains first gas supply tube 1802 and suspends first gas supply tube 1802 behind first ear 1891. Occipital head strap 1851 and sagittal head strap 1859 are connected by halo connecting strap 1849, such that sagittal head strap 1859, halo connecting strap 1849 and occipital head strap 1851 are connected in a circle about a crown of the head with occipital strap arm 1853 and sagittal strap arm 1857 extending out toward the ear. Although only one each of occipital strap arm 1853 and sagittal strap arm 1857 are shown, fastening mechanism 1803 includes a total of four straps, including a second occipital strap arm and second sagittal strap arm in the mirror image of those shown, the second occipital strap arm and second sagittal strap arm suspending second gas supply tube (not shown) above and behind a second ear in the same fashion.

Fastening mechanism 1803 is easily manufactured from a single material using a punch or die cut. In some implementations, fastening mechanism 1803 is constructed from a stretchable material such that the material conforms to the patient's head. In some implementations, fastening mechanism 1803 is constructed from hypoallergenic and/or breathable material, such as polyurethane foam, polyester or nylon fabric. In some implementations, sagittal strap clasp 1855 and occipital strap clasp 1858 are Velcro, reusable tape, or clips, or any suitable non-slip fastener to retain first gas supply tube 1802 away from first ear 1891. Sagittal strap arm 1857 is configured to pull first gas supply tube 1802 away from a top of first ear 1891, such that first gas supply tube 1802 is not in contact with first ear 1891. Occipital strap arm 1853 is configured to pull first gas supply tube 1802 away from a lower part of first ear 1891 towards the center of the nape of the neck. Nasal cannula body 1804 is affixed to the patient in this manner, without first gas supply tube 1802 contacting and irritating first ear 1891 or the sensitive skin around it. Fastening mechanism 1803 securely suspends first gas supply tube 1802 above first ear 1891, decreasing incidence of chafing, blistering, and ulcers while securing the nasal cannula body 1804 in a position on the patient.

Figure 19:
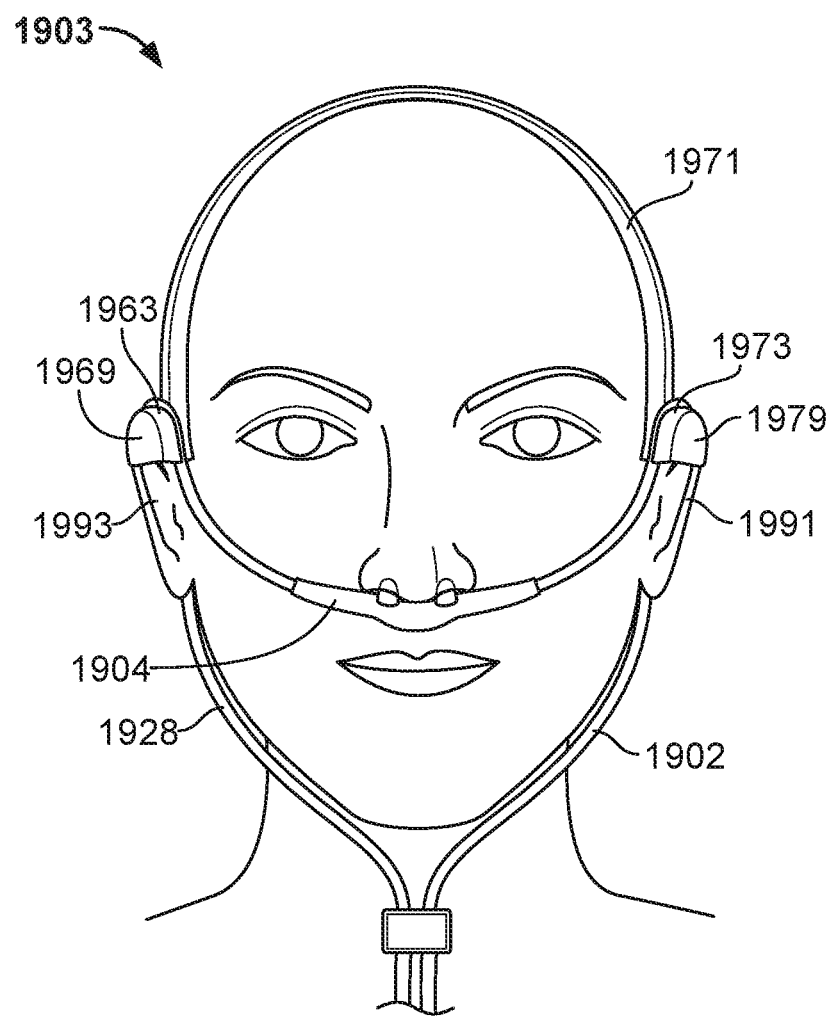
FIG. 19 shows an illustrative view of a headband for use with gas supply tubing of a nasal cannula.
Figure 20:
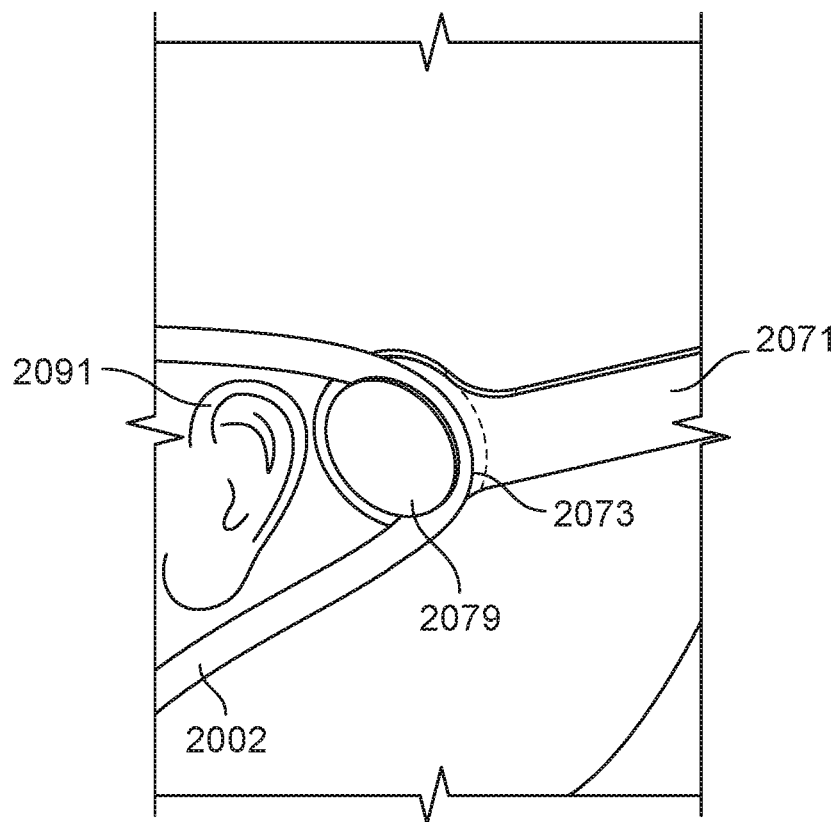
FIG. 20 shows an illustrative view of the end of a head strap for use with gas supply tubing of a nasal cannula.

FIG. 19 shows an illustrative view of a fastening mechanism 1903 including a headband 1971 for use with gas supply tubing of a nasal cannula having a raised section with a channel for retaining gas supply tubing. FIG. 20 shows a view of an end of a strap operating by a similar mechanism as the headband in FIG. 19. Fastening mechanism 1903 includes headband 1971, first band end 1917, second band end 1919, first raised section 1979 including first groove 1973, and second raised section 1969 including second groove 1963. First band end 1917 of headband 1971 comprises first raised section 1979 formed as a circular raised piece having first groove 1973 about the outside. First groove 1973 is sized to accept first gas supply tube 1902 and to retain first gas supply tube 1902 above or behind first ear 1991 of a patient. Headband 1971 is sized to retain first gas supply tube 1902 above and behind first ear 1991 on first groove 1973 of first raised section 1979 and to retain second gas supply tube 1928 above and behind second ear 1993 on second groove 1963 of second raised section 1969. Headband 1971 may be manufactured in a variety of lengths from first band end 1917 to second band end 1919, or, alternatively, may have adjustable length. First gas supply tube 1902 fluidically attached to nasal cannula body 1904 is suspended from first band end 1917 of headband 1971 where it is retained in first groove 1973 about first raised section 1979. Second gas supply tube 1928 is coupled to nasal cannula body 1904 and is suspended from second band end 1919 of headband 1971. Similarly to first gas supply tube 1902, second gas supply tube 1928 is retained in second groove 1963 about second raised section 1969. First gas supply tube 1902 and second gas supply tube 1928 are affixed to the patient's face by first groove 1973 and second groove 1963 without first gas supply tube 1902 and second gas supply tube 1928 contacting the ears. Affixation of first gas supply tube 1902, second gas supply tube 1928 and nasal cannula body 1904 to the patient without suspending first gas supply tube 1902 and second gas supply tube 1928 from first ear 1991 and second ear 1993 decreases incidence of irritation and development of MDRPU. In particular, affixation of nasal cannula body 1904 used for HFT to a patient without hot and pressurized first gas supply tube 1902 and second gas supply tube 1928 rubbing a patient's ear is important to patient comfort.

In some implementations, first groove 1973 and second groove 1963 are configured to accept wide-bore gas supply tubing, small-bore gas supply tubing or any other medical tubing. In some implementations, first groove 1973 and second groove 1963 are channel-like and maintain first gas supply tube 1902 and second gas supply tube 1928 in a position. In other implementations, first groove 1973 and second groove 1963 allow first gas supply tube 1902 and second gas supply tube 1928 to slide through first groove 1973 and second groove 1963. In some implementations, more than one headband 1971 is used to secure first gas supply tube 1902 and second gas supply tube 1928 to a patient and to suspend first gas supply tube 1902 and second gas supply tube 1928 above and behind first ear 1991 and second ear 1993 of a patient.

Similarly to fastening mechanism 1903 in FIG. 19, FIG. 20 shows a view of the end of a head strap also having a channel for securing supply tubing over an ear. FIG. 20 includes head strap 2071, first raised section 2079, first groove 2073 and first gas supply tube 2002. First gas supply tube 2002 is secured in first groove 2073 about first raised section 2079. First gas supply tube 2002 is held above first ear 2091 by head strap 2071. In some implementations, head strap 2071 is a head band similar to headband 1971 in FIG. 19. Use of head strap 2071 prevents first gas supply tube 2002 from contacting first ear 2091 and causing discomfort.

Figure 21:
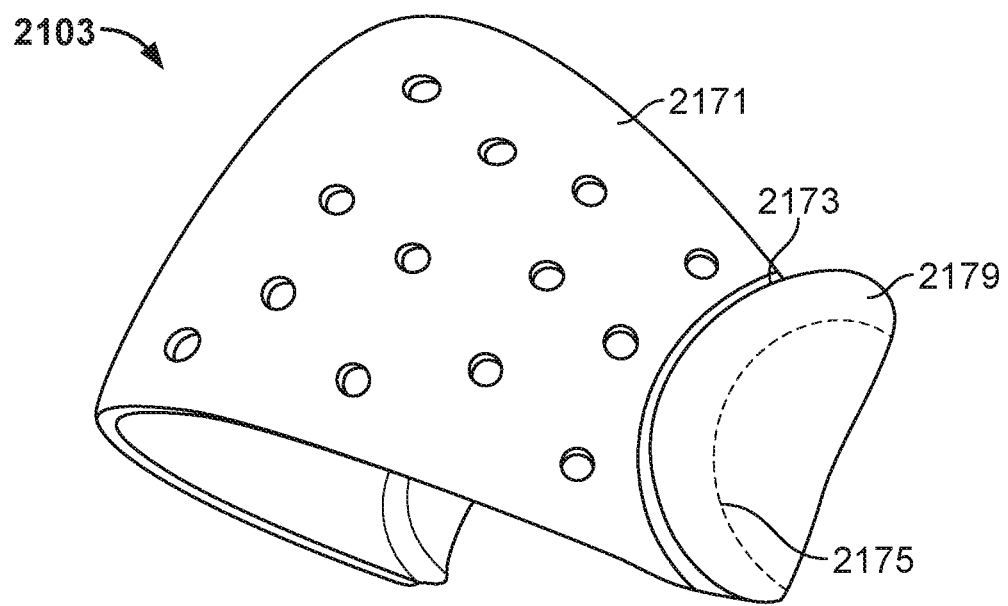
FIG. 21 shows an illustrative top view of a headband for use with gas supply tubing of a nasal cannula.

While fastening mechanism 1903 of FIG. 19 includes raised sections on which gas supply tubing is attached, in some implementations the raised sections are shaped to mimic a human ear. For example, FIG. 21 shows an illustrative top view of an alternate fastening mechanism 2103 including another embodiment of a headband 2171 with first raised section 2179 shaped like a human ear for restraining gas supply tubing of a nasal cannula above the ear of a patient. Fastening mechanism 2103 includes headband 2171, first raised section 2179, first groove 2173, and cut-out 2165. Headband 2171 includes at first band end 2117 first raised section 2179 with first groove 2173 about a top portion 2115 of first raised section 2179. First raised section 2179 also includes cut-out 2165. Headband 2171 is configured to extend over a patient's head such that first raised section 2179 is positioned above the ear of a patient. First groove 2173 in top portion 2115 of first raised section 2179 provides a channel or guide in which gas supply tubing (not shown) is restrained in order to keep the gas supply tubing from rubbing on or near the ear. In some implementations, cut-out 1165 provides space for a patient's ear. In other implementations, no cutout is required. First raised section 2179 is formed to simulate the contour of an ear, such that first raised section 2179 and first groove 2173 form a suspended artificial ear over which gas supply tubing for a nasal cannula (not shown) is looped.

The suspension of the gas supply tubing over first raised section 2179 above the patient's ear decreases the heat and friction which lead to the development of MDRPUs and increase patient comfort. First groove 2173 on first raised section 2179 supports the gas supply tubing over the patient's ear, protecting the patient's ear from friction and compression. In some implementations, headband 2171 is composed of a non-slip, flexible material which conforms to a patient's head. For example, headband 2171 may be comprised of polyethylene, high density polyethylene, polyvinyl chloride, low density polyethylene, polypropylene, polystyrene, polycarbonate, or any other suitable material. In some implementations, headband 2171 is formed as a wide band. In other implementations, headband 2171 is formed as a narrow band. In other implementations, headband 2171 is formed from a semi-rigid mesh. In other implementations, headband 2171 is formed of a stretchable material such as silicone rubber. In some implementations, headband 2171 includes perforations for enhanced air circulation at a patient's scalp. In some implementations, first raised section 2179 includes a gel pad on the patient-facing surface for enhanced comfort by reducing friction. In other implementations, headband 2171 includes comb teeth on a patient-facing surface or edge for improved placement and support on a patient's head. In some implementations, headband 2171 is adjustable. In other implementations, headband 2171 is manufactured in a variety of sizes, e.g., sizes to fit neonates, pediatric patients and adult patients.

In other implementations, headband 2171 is configured to be worn about a backside of the patient's head as an occipital support. In such implementations, an additional strap may extend from each end of headband 2171 about the forehead of the patient. The headband may be adjustable with Velcro or other closures. The placement of headband 2171 as an occipital support permits firm placement and resistance to any 'tug' of the nasal cannula gas tubing during use. First raised section 2179 may include first groove 2173 as a channel bonded to first raised section 2179.

Fastening mechanism 2103 may be used in conjunction with any respiratory therapy requiring gas supply tubing to be restrained about a patient's ears. In some implementations, fastening mechanism 2103 is used with a nasal cannula for use with an HFT system. In such implementations, first raised section 2179 and first groove 2173 suspend heated and distended gas supply tubing above a patient's ears in order to prevent rubbing and sweating that may lead to development of pressure ulcers.

Figure 22:
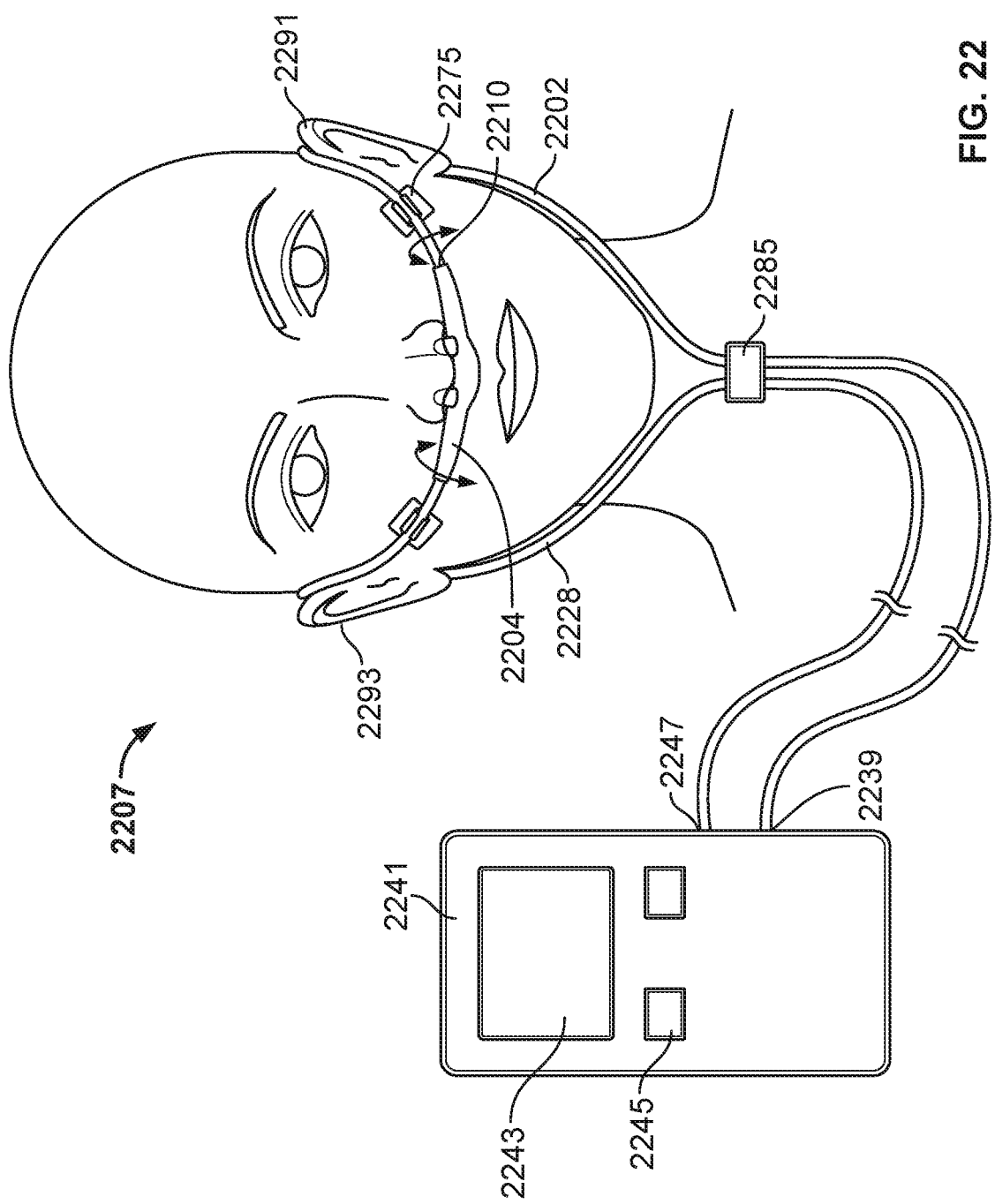
FIG. 22 shows an illustrative view of a nasal cannula system for use with high flow therapy.

The nasal cannulae and fastening devices described above can be incorporated into a respiratory therapy system, such as the illustrative respiratory therapy system 2207 shown in FIG. 22. The respiratory therapy system 2207 includes nasal cannula body 2204, first connector 2210, tubing guide 2275, first gas supply tube 2202, second gas supply tube 2228, slidable connector 2285, console 2241, display screen 2243, controls 2245, first gas supply tube port 2239, and second gas supply tube port 2247. Console 2241 includes display screen 2243 and controls 2245 that allow a user to control aspects of the respiratory therapy being delivered, such as the flow-rate of breathing gas, mixing ratio of breathing gases, administration of aerosolized medicament, or temperature of gas. Display screen 2243 may also display current settings to a user, as well as displaying warnings, for example, if there is a kink or leak in a supply tube which diminishes the gas flow. In some implementations, console 2241 includes a breathing gas source, compressor, gas blender, medicament source, or a nebulizer. In some implementations, console 2241 includes a heater and liquid reservoir. In some implementations, console 2241 controls a gas flow rate of over 8 LPM. In some implementations, console 2241 controls a gas flow rate of over 20 LPM.

Breathing gas flows from console 2241 to first gas supply tube 2202 through first gas supply tube port 2239 and from console 2241 to second gas supply tube 2228 through second gas supply tube port 2247. Breathing gas then flows through first gas supply tube 2202 and second gas supply tube 2228 to nasal cannula body 2204. First gas supply tube 2202 and second gas supply tube 2228 can be affixed to a patient's face using any fastening mechanism or combination of mechanisms described here, such as 901, 1075, 1285, 1303, 1803, 1903, or 2103 shown in FIGS. 9, 10, 12, 13, 18, 19, and 21. For example, first gas supply tube 2202 and second gas supply tube 2228 can be affixed to a patient's face with tubing guide 2275 which retains the first gas supply tube 2202 in an orientation on one of the patient's cheeks and retains second gas supply tube 2228 on the other cheek. Tubing guide 2275 allows a user to remove and replace first gas supply tube 2202 and second gas supply tube 2228 such that when first gas supply tube 2202 and second gas supply tube 2228 is replaced in tubing guide 2275, first gas supply tube 2202 and second gas supply tube 2228 are placed into a proper orientation with respect to the nasal cannula body 2204 and facial anatomy of the patient. First gas supply tube 2202 and second gas supply tube 2228 are shown draped over first ear 2091 and second ear 2093 of the patient, but in other implementations first gas supply tube 2202 and second gas supply tube 2228 can be used with any other fastening mechanism to keep the first gas supply tube 2202 and second gas supply tube 2228 away from sensitive skin surrounding a patient's ears.

In another example, first gas supply tube 2202 and second gas supply tube 2228 of respiratory therapy system 2207 can be coupled to nasal cannula body 2204 at first connector 2210, such as swivel connector 901, which permits rotation and swivel motions such that movement of first gas supply tube 2202 and second gas supply tube 2228 is not transferred to nasal cannula body 2204. Thus, nasal cannula body 2204 is maintained in a proper positioning despite motion or movement of first gas supply tube 2202 and second gas supply tube 2228. First gas supply tube 2202 and second gas supply tube 2228 can also be used with slidable connector 2285, similar to slidable connector 1285, to retain first gas supply tube 2202 and second gas supply tube 2228 under the chin of the patient to securely affix the nasal cannula body 2204 to the patient's face while keeping the first gas supply tube 2202 and second gas supply tube 2228 from kinking.

Furthermore, respiratory therapy system 2207 may be used with any of the previously described nasal cannulae, including 100, 200, 300, 500, 700, and 800 described in FIGS. 1, 2, 3, 5, 7, and 8. Respiratory therapy system 2207 may be used with a nasal cannula body 2204 that allows a rotation of nasal prongs such that the position of the nasal prong in a patient's nare is adjustable to account for differences in nasal anatomy or nare size. The adjustment of nasal prong positioning permits the administration of respiratory therapy without the discomfort to the patient associated with contact of the nasal prongs with sensitive tissues in the nare or the misdirected flow of breathing gas onto nasal tissues.

The appropriate orientation of nasal prongs in a patient's nares and the secure affixing of the nasal cannula and gas supply tubes in proper position allow respiratory therapy system 2207 to provide effective therapy to a patient. Correctly directing breathing gas, and, in particular, heated and humidified breathing gas for HFT, into the nasal passageway promotes flushing of the upper respiratory passageways for therapeutic effect. The appropriate orientation of the nasal prongs in the nares also decreases patient discomfort associated with poor positioning leading to rubbing or contact of the nasal prongs in the nare or irritation of the mucosa due to misdirected breathing gas flow. Restraining supply gas tubing and securing the positioning of the nasal cannula further increases the occurrence of successful therapeutic outcomes. Supply gas tubing restraints which protect the sensitive tissues surrounding the ears from irritation and development of ulcers increase patient comfort and patients are less likely to move or adjust gas supply tubes which are not causing irritation. These devices improve therapeutic outcomes by ensuring that effective respiratory therapy is delivered to a patient.

The foregoing is merely illustrative of the principles of the disclosure, and the apparatuses can be practiced by other than the described embodiments, which are presented for purposes of illustration and not of limitation. It is to be understood that the apparatuses disclosed herein, while shown for use in high flow therapy systems, may be applied to systems to be used in other ventilation circuits.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

We claim:

1. A nasal cannula for respiratory therapy, the cannula comprising:
   a first gas supply tube having a distal end that terminates in a first connector;
   a second gas supply tube having a distal end that terminates in a second connector;
   a nasal cannula body comprising:
      a first end coupled to the first connector,
      a second end, opposite the first end,
      a longitudinal axis extending from the first end to the second end,
      a first nasal prong in fluid communication with the first gas supply tube;
      a second nasal prong;
      a first section and a second section, the first section and the second section disposed adjacently along the longitudinal axis of the nasal cannula body, the first nasal prong disposed on the first section and the second nasal prong disposed on the second section, the first section and the second section coupled by a journal bearing such that the first section is rotatable about the longitudinal axis of the nasal cannula body relative to the second section;
   a first elastomeric loop having a first over ear connector detachably coupled to the first gas supply tube, the first over ear connector coupled non-fluidically to the first gas supply tube, wherein the first elastomeric loop is sized to hang over a first ear; and
   a second elastomeric loop having a second over ear connector detachably coupled to the second gas supply tube, the second over ear connector coupled non-fluidically to the second gas supply tube, wherein the second elastomeric loop is sized to hang over a second ear.

2. The nasal cannula of claim 1, wherein the first end of the nasal cannula body is rotatably coupled to the first connector, and
   wherein the first nasal prong is rotatable relative to the first gas supply tube, the rotation being about the longitudinal axis of the nasal cannula body.

3. The nasal cannula of claim 2, wherein the rotatable coupling between the first end of the nasal cannula body and the first connector is a journal bearing.

4. The nasal cannula of claim 3, wherein the journal bearing has sufficient static frictional torque to maintain a rotational position of the first nasal prong relative to the first gas supply tube.

5. The nasal cannula of claim 4, wherein the journal bearing has frictional torque of about 0.01 Nm to 1 Nm.

6. The nasal cannula of claim 3, wherein the journal bearing has an internal surface contoured such that the journal bearing has intermittent rotational stops.

7. The nasal cannula of claim 2, further comprising a lock configured to lock a rotational position of the first nasal prong relative to the first gas supply tube.

8. The nasal cannula of claim 1, wherein the second nasal prong is rotatable relative to the first gas supply tube, the rotation being about the longitudinal axis of the nasal cannula body.

9. The nasal cannula of claim 1, wherein the first nasal prong is rotatable relative to the second nasal prong about the longitudinal axis of the nasal cannula body.

10. The nasal cannula of claim 1, wherein the second end of the nasal cannula body is rotatably coupled to the second connector, and wherein the second nasal prong is in fluid communication with the second gas supply tube.

11. The nasal cannula of claim 1, wherein the first nasal prong is not in fluid communication with the second nasal prong.

12. The nasal cannula of claim 1, wherein the first nasal prong and the second nasal prong are joined by a solid bridge connector.

13. The nasal cannula of claim 1, wherein an axial distance between the first nasal prong and the second nasal prong along the longitudinal axis of the nasal cannula body is adjustable.

14. The nasal cannula of claim 13, wherein the first nasal prong is axially slidable along the longitudinal axis of the nasal cannula body relative to the second nasal prong.

15. The nasal cannula of claim 14, wherein the nasal cannula body includes a surface contoured to provide a discrete number of stable axial positions of the first nasal prong.

16. The nasal cannula of claim 1, wherein the nasal cannula body is detachable from the first gas supply tube.

17. The nasal cannula of claim 1, further comprising a gas source, wherein the gas source is configured to provide breathing gas at a flow rate of over 8 liters per minute (LPM).

18. The nasal cannula of claim 1, wherein the first connector includes a first section sized to receive the first gas supply tube and a second section sized for insertion into the first end of the nasal cannula body, the first section coupled to the second section at a bearing, wherein the second section is configured to swivel relative to the first section.

19. The nasal cannula of claim 1, wherein the first elastomeric loop is configured to be coupled to the first gas supply tube at a first coupler configured to be positioned at a bottom point of the first elastomeric loop; and
   wherein the second elastomeric loop is configured to be coupled to the second gas supply tube at a second coupler configured to be positioned at a bottom point of the second elastomeric loop.

20. The nasal cannula of claim 19, wherein the first coupler is configured as a column having openings at either end sized to fit an outer diameter of the first gas supply tube; and
   wherein the second coupler is configured as a column having openings at either end sized to fit an outer diameter of the second gas supply tube.

21. The nasal cannula of claim 1, wherein the first elastomeric loop and the second elastomeric loop each comprise a loop encasement covering the elastomeric loop and configured to be disposed between the elastomeric loop and the patient's ear.

22. The nasal cannula of claim 21, wherein the loop encasement comprises a fluid-filled cushion or a foam.

* * * * *